United States Patent
Okay

(10) Patent No.: US 9,968,547 B2
(45) Date of Patent: *May 15, 2018

(54) COMPOSITIONS FOR TREATMENT OF XEROSTOMIA AND FOR TOOTH TREATMENT

(71) Applicant: 3 IN 1 DENTAL PLLC, New York, NY (US)

(72) Inventor: Devin J. Okay, Mamaroneck, NY (US)

(73) Assignee: 3 IN 1 DENTAL PLLC, New York, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/695,958

(22) Filed: Apr. 24, 2015

(65) Prior Publication Data

US 2015/0231060 A1    Aug. 20, 2015

Related U.S. Application Data

(63) Continuation-in-part of application No. PCT/US2014/026238, filed on Mar. 13, 2014.

(60) Provisional application No. 61/783,194, filed on Mar. 14, 2013.

(51) Int. Cl.
  *A61K 8/98*    (2006.01)
  *A61K 8/02*    (2006.01)
  *A61K 8/66*    (2006.01)

(52) U.S. Cl.
  CPC ............ *A61K 8/981* (2013.01); *A61K 8/0233* (2013.01); *A61K 8/66* (2013.01)

(58) Field of Classification Search
  CPC ......... A61K 8/891; A61K 8/0233; A61K 8/66
  See application file for complete search history.

(56) References Cited

U.S. PATENT DOCUMENTS

| 4,327,079 A | * | 4/1982 | Aoki | A61Q 11/00 424/49 |
| 5,214,180 A | | 5/1993 | Ferrari et al. | |
| 5,431,924 A | | 6/1995 | Ghosh et al. | |
| 5,545,668 A | | 8/1996 | Skubitz et al. | |
| 6,162,447 A | * | 12/2000 | Fankhauser | A61K 8/068 424/401 |
| 6,200,551 B1 | | 3/2001 | Morgan | |

(Continued)

FOREIGN PATENT DOCUMENTS

| CN | 1893917 A | 1/2007 |
| CN | 101288722 | 10/2008 |

(Continued)

OTHER PUBLICATIONS

International Search Report dated Aug. 8, 2014, in connection with PCT International Application No. PCT/US14/26238 (attached hereto as Exhibit 1).

(Continued)

*Primary Examiner* — Jianfeng Song
(74) *Attorney, Agent, or Firm* — Cooper & Dunham, LLP

(57) ABSTRACT

The present application provides an oral care composition comprising:
  a) one or more omega fatty acids;
  and one or more of the following:
  b) one or more emulsifying agents;
  c) one or more protease enzymes;
  d) one or more soluble calcium phosphate remineralizing agents;
  e) one or more amino acids.

6 Claims, 2 Drawing Sheets

(56) References Cited

U.S. PATENT DOCUMENTS

| | | | |
|---|---|---|---|
| 6,331,291 B1 | 12/2001 | Glace et al. | |
| 6,729,878 B2 | 5/2004 | Cohen et al. | |
| 8,173,711 B2 | 5/2012 | Saito et al. | |
| 8,540,970 B2* | 9/2013 | Rodriguez-Vilaboa | A61K 8/046 424/48 |
| 2002/0012648 A1 | 1/2002 | Orthoefer | |
| 2002/0028251 A1* | 3/2002 | Okay | A61K 8/20 424/498 |
| 2005/0008584 A1* | 1/2005 | Montgomery | A61K 8/02 424/53 |
| 2005/0032757 A1 | 2/2005 | Cho | |
| 2005/0137109 A1* | 6/2005 | Quan | A61K 8/0208 510/303 |
| 2005/0143274 A1 | 6/2005 | Ghosh et al. | |
| 2005/0244347 A1 | 11/2005 | Mehra et al. | |
| 2006/0020031 A1 | 1/2006 | Berlin | |
| 2006/0177383 A1 | 8/2006 | Gebreselassie et al. | |
| 2006/0292090 A1 | 12/2006 | Sharma et al. | |
| 2007/0104783 A1 | 5/2007 | Domb et al. | |
| 2007/0154591 A1* | 7/2007 | Andersen | A23G 4/06 426/3 |
| 2007/0258916 A1* | 11/2007 | Ferracane | A61K 8/25 424/57 |
| 2008/0057116 A1* | 3/2008 | Pleva | A61K 8/925 424/456 |
| 2008/0299050 A1* | 12/2008 | Bortz | A61K 31/415 424/49 |
| 2008/0317703 A1 | 12/2008 | Kawa et al. | |
| 2009/0186057 A1 | 7/2009 | Farmer et al. | |
| 2009/0202451 A1* | 8/2009 | Prencipe | A61K 8/25 424/50 |
| 2009/0220642 A1* | 9/2009 | Boghani | A23G 4/066 426/5 |
| 2010/0098791 A1 | 4/2010 | Rodriguez-Vilaboa | |
| 2010/0143271 A1* | 6/2010 | Yang | A61K 8/24 424/52 |
| 2010/0255119 A1 | 10/2010 | Schneid | |
| 2010/0291162 A1* | 11/2010 | Haas | A61K 8/0216 424/401 |
| 2011/0189110 A1 | 8/2011 | Kohli et al. | |
| 2011/0300241 A1 | 12/2011 | Hsu | |
| 2012/0034280 A1 | 2/2012 | Cohen et al. | |
| 2012/0070423 A1 | 3/2012 | Nanda | |
| 2012/0175273 A1* | 7/2012 | Jacobs | A61Q 11/00 206/63.5 |
| 2013/0017240 A1* | 1/2013 | Porter | A61K 8/27 424/401 |
| 2015/0290107 A1 | 10/2015 | Okay | |

FOREIGN PATENT DOCUMENTS

| | | |
|---|---|---|
| CN | 101554381 A | 10/2009 |
| DE | 102008023014 A1 | 11/2009 |
| EP | 1025841 B1 | 6/2002 |
| EP | 2027852 A1 | 2/2009 |
| EP | 1906920 A2 | 3/2011 |
| WO | WO 2001/13956 A2 | 3/2001 |
| WO | WO 2001/64175 A1 | 9/2001 |
| WO | 2005058267 A1 | 6/2005 |
| WO | WO 2007/010430 A1 | 1/2007 |
| WO | WO 2007/010430 A2 | 1/2007 |
| WO | 2014160285 A1 | 10/2014 |

OTHER PUBLICATIONS

Written Opinion of International Search Authority dated Aug. 8, 2014, in connection with PCT International Application No. PCT/US14/26238 (attached hereto as Exhibit 2).

Chattopadhyay, S., et al., "Role of oral glutamine in alleviation and prevention of radiation-induced oral mucositis: A prospective randomized study," South Asian Journal of Cancer, 3(1): 8-12, Jan.-Mar. 2014 (attached hereto as Exhibit 3).

Vanichvatana, S., et al., "Efficacy of two calcium phosphate pastes on the remineralization of artificial caries: a randomized controlled double-blind in situ study," International Journal of Oral Science, 5 224-228, (2013) (attached hereto as Exhibit 4).

Search History of PCT/US14/026238 dated Jul. 15, 2014, in connection with PCT International Application No. PCT/US14/26238 (attached hereto as Exhibit 5).

Extended European Search Report, including Supplementary Search Report and European Search Opinion, in connection with European Patent Application No. 14776375.9, dated Jul. 8, 2016.

Office Action dated Apr. 5, 2016 in connection with U.S. Appl. No. 14/438,507.

Final Office Action dated Feb. 6, 2017 in connection with U.S. Appl. No. 14/438,507.

Official Action dated Apr. 19, 2017 in connection with Eurasian Patent Application No. 201591755 including English language.

Gullapalli et al. (1996) International Journal of Pharmaceutics, 140, 97-109.

Divya et al. (2011) Journal of Applied Pharmaceutical Science, 01 (08), 43-47.

Office Action dated Sep. 20, 2017 in connection with U.S. Appl. No. 14/438,507.

Office Action dated May 15, 2017 in connection with Chinese Patent Application No. 201480014308.X including English language translation.

\* cited by examiner

Bilayer Tablet → Rapidly Disintegreting Upper Layer → Slowly Eroding Lower Layer Bilayer Tablet Rapidly
Disintegreting Outer Layer Slowly Eroding Core

COMPOSITIONS FOR TREATMENT OF XEROSTOMIA AND FOR TOOTH TREATMENT

This application is a continuation-in-part of and claims priority of PCT International Application No. PCT/US2014/026238, filed Mar. 13, 2014, which claims the benefit of U.S. Provisional Application No. 62/783,194, filed Mar. 14, 2013, the contents of each of which are hereby incorporated by reference in their entirety.

Throughout this application, certain publications are referenced in parentheses. Full citations for these publications may be found immediately preceding the claims. The disclosures of these publications in their entireties are hereby incorporated by reference into this application.

BACKGROUND

Xerostomia is the subjective sensation of dry mouth and may be associated with diminished or deficient salivary secretion. Saliva and salivary flow help prevent the accumulation of microorganisms in the mouth (Nederfors et al. 1997). Saliva is also necessary for effective remineralization of teeth (Narhi et al. 1999). Salivary flow initiates digestion of foods and help dissolve and remove food particles from the mouth. Saliva also lubricates the mucosa of the mouth, facilitating speech, eating, and swallowing and preventing mechanical injury to the surfaces of the mouth. Xerostomia is a commonly occurring disorder and results in higher risk for oral complications.

Diverse symptoms and consequences have been associated with xerostomia. Symptoms include halitosis, soreness, oral burning, difficulty swallowing, and altered taste sensation. Xerostomia also causes dental disorders including oral mucous membrane ulcers, dental caries and periodontosis, oral infections and respiratory tract infections.

Known causes of xerostomia include various diseases causing organic change of salivary glands; pathological changes of salivary glands caused by systemic diseases; damaged salivary glands owing to radiotherapy; HIV infection (AIDS); secretory hypofunction owing to aging; and effects of administration of various drugs. Mental fatigue or stress may also be factors. Various drugs also result in xerostomia as a side effect. Examples of drugs that may cause xerostomia include: diuretics such as trichloromethiazide and furosemide, hypotensors such as reserpine and clonidine hydrochloride, anticholinergic agents such as atropine sulfate, and antihistamines such as chlorphenylamine maleate. Other examples thereof include various expectorant/cough suppressants, anti-Parkinson drugs, psychotropic drugs, antidepressants, tranquilizers, muscle relaxants, opiates and other narcotics. Radiotherapy has become increasingly important for treating malignant tumors in oral surgery and otolaryngology fields, and almost inevitably causes damage to salivary glands by ionizing radiation. This damage can result in especially severe xerostomia. Medications are believed to be responsible for a significant proportion of cases of xerostomia, particularly in the elderly (Nedefors et al. 1997). The list of drugs that are believed to affect saliva levels includes more than 400 agents (Narhi et al. 1999).

Xerostomia is more common among older people and among women (Hochberg et al. 1998; Nederfors et al. 1997). In one study xerostomia was reputed in 21.3% of the men and in 27.3% of women (Nederfors et al. 1996). In another study of elderly type-2 diabetic individuals, the prevalence of dry mouth was found to be 25% (Borges B C et al. 2010). The prevalence of xerostomia in varied populations ranges from 0.9% to 46% (Orellana, M. F. et al. 2006).

There are various therapies for the treatment of xerostomia, although many result in unfavorable side effects and limited efficacy (Cassolato, S. F. et al. 2003; Gupta, A. et al. 2006; Silvestre-Donat, F. J. et al. 2004). For example, malic and citric acid have been used as salivary stimulants. However, they had a demineralizing effect on tooth enamel (Anneroth, G. et al. 1980; Davies, A. N. 2000).

SUMMARY

The present application provides an oral care composition comprising:
a) emu oil;
and one or more of the following:
b) one or more emulsifying agents;
c) one or more protease enzymes;
d) one or more soluble calcium phosphate remineralizing agents;
e) one or more amino acids.

The present application provides an oral care composition comprising:
a) one or more omega fatty acids;
and one or more of the following:
b) one or more emulsifying agents;
c) one or more protease enzymes;
d) one or more soluble calcium phosphate remineralizing agents;
e) one or more amino acids.

DETAILED DESCRIPTION

Figure 1:
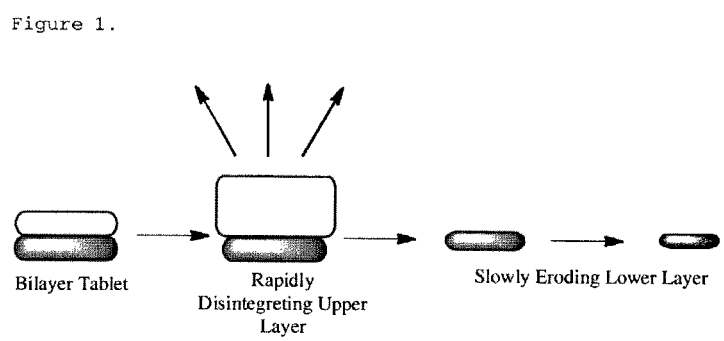
FIG. 1. Bilayer Tablet comprising a rapidly disintegrating layer and a slowly eroding layer.

The present application provides an oral care composition comprising:
a) emu oil;
and one or more of the following:
b) one or more emulsifying agents;
c) one or more protease enzymes;
d) one or more soluble calcium phosphate remineralizing agents;
e) one or more whitening agents.

In one embodiment, the composition comprising:
a) emu oil;
and two or more of the following:
b) one or more emulsifying agents;
c) one or more protease enzymes;
d) one or more soluble calcium phosphate remineralizing agents;
e) one or more whitening agents.

In one embodiment, the composition comprising:
a) emu oil;
and three or more of the following:
b) one or more emulsifying agents;
c) one or more protease enzymes;
d) one or more soluble calcium phosphate remineralizing agents;
e) one or more whitening agents.

In one embodiment, the composition comprising:
a) emu oil;
b) one or more emulsifying agents;
c) one or more protease enzymes;
d) one or more soluble calcium phosphate remineralizing agents;
e) one or more whitening agents.

In one embodiment, an oral care composition consisting essentially of
a) emu oil;
and one or more of the following:
b) one or more emulsifying agents;
c) one or more protease enzymes;
d) one or more soluble calcium phosphate remineralizing agents;
e) one or more whitening agents.

In one embodiment, the composition consisting essentially of:
a) emu oil;
and two or more of the following:
b) one or more emulsifying agents;
c) one or more protease enzymes;
d) one or more soluble calcium phosphate remineralizing agents;
e) one or more whitening agents.

In one embodiment, the composition consisting essentially of:
a) emu oil;
and three or more of the following:
b) one or more emulsifying agents;
c) one or more protease enzymes;
d) one or more soluble calcium phosphate remineralizing agents;
e) one or more whitening agents.

In one embodiment, the composition consisting essentially of:
a) emu oil;
b) one or more emulsifying agents;
c) one or more protease enzymes;
d) one or more soluble calcium phosphate remineralizing agents;
e) one or more whitening agents.

In one embodiment, the composition wherein one or more of the protease enzymes are selected from the group consisting of papain, trypsin, chymotrypsin, aminopeptidase, carboxypeptidase, pepsin, and cathepsin.

In one embodiment, the protease enzyme is stem bromelain. The stem bromelain provides an anti-inflammatory effect.

In one embodiment, 50 mg of stem bromelain present in the composition.

In one embodiment, the composition wherein the one or more whitening agents are selected from the group consisting of carbamide peroxide and hydrogen peroxide.

In one embodiment, the composition wherein the one or more soluble calcium phosphate remineralizing agents are selected from the group consisting of dibasic calcium phosphate, monocalcium phosphate, tricalcium phosphate, and tetracalcium phosphate.

In one embodiment, the composition wherein the soluble calcium phosphate remineralizing agent is amorphous calcium phosphate.

In one embodiment, the composition wherein the one or more emulsifying agents are phospholipids.

In one embodiment, the composition wherein the phospholipids are lecithin.

In one embodiment, the composition wherein the lecithin is dairy-free and/or egg-free. A dairy-free or egg-free lecithin provides a composition with a longer shelf life in comparison to lecithin sourced from egg or milk.

In one embodiment, the composition wherein the lecithin is soy lecithin. In one embodiment, the composition wherein the lecithin is sourced from soybeans.

In one embodiment, the composition wherein the composition further comprises an isomalt.

In one embodiment, the composition wherein the isomalt is selected from the group consisting of galenIQ™ 720 and galenIQ™ 721.

In one embodiment, the composition wherein the composition further comprises a disintegrating agent.

In one embodiment, the composition wherein the disintegrating agent is crospovidone.

In one embodiment, the composition wherein the composition further comprises magnesium stearate.

In one embodiment, the composition wherein the composition further comprises glycerin.

In one embodiment, the composition wherein the composition further comprises fluoride.

In one embodiment, the composition wherein the remineralizing agent is white in color.

In one embodiment, the composition is formulated as a tablet, a bilayer tablet, a multilayer tablet, chewing gum, a toothpaste, a lozenge, a powder, a gel, a viscous gel, an ointment, a cream, a liquid, a mouthwash, or a candy.

In one embodiment, the composition is formulated as a round flat tablet or a round concave tablet or a round convex tablet. The tablet may have a bevel edge.

In one embodiment, the composition is formulated as a bilayer tablet.

In one embodiment, the composition wherein the bilayer tablet comprises a rapidly disintegrating layer and a slowly eroding layer.

In one embodiment, the composition wherein the one or more whitening agents are present only in the rapidly disintegrating layer.

In one embodiment, the composition wherein the emu oil and the one or more proteases are present only in the slowly eroding layer.

In one embodiment, the composition wherein the one or more whitening agents are present only in the rapidly disintegrating layer; and the emu oil and the one or more proteases are present only in the slowly eroding layer.

In one embodiment, the composition wherein the rapidly disintegrating layer comprises carbamide peroxide in an amount between 0.1 to 10.0% by weight.

In one embodiment, the composition wherein the rapidly disintegrating layer comprises carbamide peroxide in an amount of 1.0% by weight.

In one embodiment, the composition wherein the slowly eroding layer comprises emu oil in an amount between 0.1 to 15% by weight.

In one embodiment, the composition wherein the slowly eroding layer comprises emu oil in an amount of 10% by weight.

In one embodiment, the composition wherein the slowly eroding layer comprises papain in an amount between 0.1 to 20% by weight.

In one embodiment, the composition wherein the slowly eroding layer comprises papain in an amount of 10% by weight.

The present application provides a method of treating a subject suffering from xerostomia which comprises administering to the subject, in an amount effective to treat the xerostomia, a composition of the present application.

In one embodiment, the method wherein the composition further whitens teeth in the subject's mouth.

In one embodiment, the method wherein the composition further remineralizes teeth in the subject's mouth.

In one embodiment, the method wherein the composition further whitens and remineralizes teeth in the subject's mouth.

In one embodiment, the method wherein the composition further reduces dental sensitivity of the subject.

In one embodiment, the method wherein the composition further treats dental caries of the subject.

In one embodiment, the method wherein the subject is a human.

In one embodiment, the method wherein the subject is a non-human animal.

In one embodiment, the method wherein the subject has an autoimmune disease, diabetes, Sjögren's syndrome, or has recently undergone radiation therapy or chemotherapy.

In one embodiment, the method wherein the subject is concurrently taking one or more medications that causes xerostomia.

The present application provides an oral care composition for whitening teeth comprising one or more whitening agents, wherein the composition is formulated as a bilayer tablet comprising:
(i) a rapidly disintegrating layer; and
(ii) a slowly eroding layer,
wherein the one or more whitening agents are each oxidizing agents and are each present only in the rapidly disintegrating layer.

In one embodiment, an oral care composition for whitening teeth consisting essentially of one or more whitening agents, wherein the composition is formulated as a bilayer tablet comprising:
(i) a rapidly disintegrating layer; and
(ii) a slowly eroding layer,
wherein the one or more whitening agents are each oxidizing agents and are each present only in the rapidly disintegrating layer. In one embodiment of the bilayer composition, the composition wherein the one or more whitening agents are selected from the group consisting of carbamide peroxide and hydrogen peroxide.

In one embodiment of the bilayer composition, the composition wherein the whitening agent is carbamide peroxide and is present in an amount between 0.1 to 10.0% by weight of the disintegrating layer.

In one embodiment of the bilayer composition, the composition wherein the whitening agent is carbamide peroxide and is present in an amount of 1.0% by weight of the disintegrating layer.

In one embodiment of the bilayer composition, the composition further comprising one or more of the following:
a) emu oil;
b) one or more emulsifying agents;
c) one or more protease enzymes;
d) one or more soluble calcium phosphate remineralizing agents.

In one embodiment of the bilayer composition, the composition further comprising two or more of the following:
a) emu oil;
b) one or more emulsifying agents;
c) one or more protease enzymes;
d) one or more soluble calcium phosphate remineralizing agents.

In one embodiment of the bilayer composition, the composition further comprising three or more of the following:
a) emu oil;
b) one or more emulsifying agents;
c) one or more protease enzymes;
d) one or more soluble calcium phosphate remineralizing agents.

In one embodiment of the bilayer composition, the composition further comprising each of the following:
a) emu oil;
b) one or more emulsifying agents;
c) one or more protease enzymes;
d) one or more soluble calcium phosphate remineralizing agents.

In one embodiment of the bilayer composition, the composition further comprising each of the following:
a) emu oil;
and one or more of the following:
b) one or more emulsifying agents;
c) one or more protease enzymes;
d) one or more soluble calcium phosphate remineralizing agents.

In one embodiment of the bilayer composition, the composition wherein the emu oil, the one or more emulsifying agents, and the one or more protease enzymes are present only in the slowly eroding layer.

In one embodiment of the bilayer composition, the composition wherein the one or more soluble calcium phosphate remineralizing agents are present only in the rapidly disintegrating layer.

The present application provides a method of treating a subject suffering from xerostomia which comprises administering to the subject, in an amount effective to treat the xerostomia, a bilayer composition of the present application.

In one embodiment, the method wherein the bilayer composition further whitens teeth in the subject's mouth.

In one embodiment, an oral care composition comprising:
a) a whitening agent;
and one or more of the following:
b) one or more emulsifying agents;
c) one or more protease enzymes; and
d) one or more soluble calcium phosphate remineralizing agents.

In one embodiment, an oral care composition comprising:
a) emu oil;
and one or more of the following:
b) one or more emulsifying agents;
c) one or more protease enzymes; and
d) one or more soluble calcium phosphate remineralizing agents.

In one embodiment, an oral care composition consisting essentially of:
a) a whitening agent;
and one or more of the following:
b) one or more emulsifying agents;
c) one or more protease enzymes; and
d) one or more soluble calcium phosphate remineralizing agents.

In one embodiment, an oral care composition consisting essentially of:
a) emu oil;
and one or more of the following:
b) one or more emulsifying agents;
c) one or more protease enzymes; and
d) one or more soluble calcium phosphate remineralizing agents.

The present application provides a package comprising:
i) a first oral care composition comprising:
a) a whitening agent;
and one or more of the following:
b) one or more emulsifying agents;
c) one or more protease enzymes; and
d) one or more soluble calcium phosphate remineralizing agents;
ii) a second oral care composition comprising
a) emu oil;
and one or more of the following:
b) one or more emulsifying agents;
c) one or more protease enzymes; and
d) one or more soluble calcium phosphate remineralizing agents; and
iii) instruction for use of the first oral care composition and second oral care composition to treat a subject afflicted with mucositis or xerostomia.

The present application provides a package consisting essentially of:
i) a first oral care composition comprising:
a) a whitening agent;
and one or more of the following:
b) one or more emulsifying agents;
c) one or more protease enzymes; and
d) one or more soluble calcium phosphate remineralizing agents;
ii) a second oral care composition comprising:
a) emu oil;
and one or more of the following:
b) one or more emulsifying agents;
c) one or more protease enzymes; and
d) one or more soluble calcium phosphate remineralizing agents; and
iii) instruction for use of the first oral care composition and second oral care composition to treat a subject afflicted with mucositis or xerostomia.

The present application provides a therapeutic package for dispensing to, or for use in dispensing to, a subject afflicted with mucositis or xerostomia, which comprises:
i) a first oral care composition comprising:
a) a whitening agent;
and one or more of the following:
b) one or more emulsifying agents;
c) one or more protease enzymes; and
d) one or more soluble calcium phosphate remineralizing agents;
ii) a second oral care composition comprising:
a) emu oil;
and one or more of the following:
b) one or more emulsifying agents;
c) one or more protease enzymes; and
d) one or more soluble calcium phosphate remineralizing agents; and
iii) labeling directing the use of said package in the treatment of said subject.

The present application provides a therapeutic package for dispensing to, or for use in dispensing to, a subject afflicted with mucositis or xerostomia, which consists essentially of:
i) a first oral care composition comprising:
a) a whitening agent;
and one or more of the following:
b) one or more emulsifying agents;
c) one or more protease enzymes; and
d) one or more soluble calcium phosphate remineralizing agents;
ii) a second oral care composition comprising:
a) emu oil;
and one or more of the following:
b) one or more emulsifying agents;
c) one or more protease enzymes; and
d) one or more soluble calcium phosphate remineralizing agents; and
iii) labeling directing the use of said package in the treatment of said subject.

The present application provides a method of treating a subject afflicted with mucositis or xerostomia comprising administering a first oral care composition followed by one or more of a second oral care composition.

The present application provides a method treating a subject afflicted with mucositis or xerostomia consisting essentially of administering a first oral care composition followed by one or more of a second oral care composition.

The present application provides a method treating a subject afflicted with mucositis or xerostomia comprising administering a single first oral care composition followed by five of a second oral care composition.

The present application provides a method treating a subject afflicted with mucositis or xerostomia consisting essentially of administering a single first oral care composition followed by five of a second oral care composition.

In one embodiment, the first oral care composition comprises:
a) a whitening agent;
and one or more of the following:
b) one or more emulsifying agents;
c) one or more protease enzymes; and
d) one or more soluble calcium phosphate remineralizing agents; and
the second oral care composition comprises:
a) emu oil;
and one or more of the following:
b) one or more emulsifying agents;
c) one or more protease enzymes; and
d) one or more soluble calcium phosphate remineralizing agents.

In one embodiment, the first oral care composition consists essentially of:
a) a whitening agent;
and one or more of the following:
b) one or more emulsifying agents;
c) one or more protease enzymes; and
d) one or more soluble calcium phosphate remineralizing agents; and
the second oral care composition consists essentially of:
a) emu oil;
and one or more of the following:
b) one or more emulsifying agents;
c) one or more protease enzymes; and
d) one or more soluble calcium phosphate remineralizing agents.

In one embodiment the first oral care composition and the one or more of a second oral care compositions are administering over 24 hours.

In one embodiment, the package is a sealed package.

In one embodiment, the sealed package is a blister pack.

In one embodiment, the blister pack contains one of the first oral care composition and five of the second oral care composition.

In one embodiment, the first oral care composition further comprises isomalt.

In one embodiment, the first oral care composition further comprises sucralose.

In one embodiment, the second oral care composition further comprises potassium nitrate.

In one embodiment, the first oral care composition is a tablet. In one embodiment, the tablet is an 800 mg tablet. In one embodiment, the tablet is a 1000 mg tablet.

In one embodiment, the second oral care composition is a tablet. In one embodiment, the tablet is an 800 mg tablet. In one embodiment, the tablet is a 1000 mg tablet.

In yet another embodiment, the tablet is a 2 g tablet and the tablet is 20 mm in diameter.

In one embodiment, the whitening agent is carbamide peroxide. In one embodiment, the amount of carbamide peroxide in the tablet is 1 mg-5 mg. In one embodiment, the amount of carbamide peroxide in the tablet is 1 mg-4 mg. In one embodiment, the amount of carbamide peroxide in the tablet is 2 mg-3 mg. In one embodiment, the amount of carbamide peroxide in the tablet is 1 mg. In one embodiment, the amount of carbamide peroxide in the tablet is 2 mg. In one embodiment, the amount of carbamide peroxide in the tablet is 2.5 mg.

In one embodiment, the emulsifying agent is soy lecithin. In one embodiment, the concentration of the soy lecithin is between 1 to 5% by weight. In one embodiment, the concentration of the soy lecithin is between 2 to 5% by weight.

In one embodiment, the soluble calcium phosphate remineralizing agent is tricalcium phosphate. In one embodiment, the concentration of the tricalcium phosphate is between 1 to 10% by weight. In one embodiment, the concentration of the tricalcium phosphate is between 3 to 10% by weight. In one embodiment, the concentration of the tricalcium phosphate is 10% by weight.

In one embodiment, the concentration of the emu oil is between 5 to 10% by weight. In one embodiment, the concentration of the emu oil is between 5 to 7% by weight. In one embodiment, the concentration of the emu oil is 6% by weight.

In one embodiment, the protease enzyme is stem bromelain. In one embodiment, the amount of stem bromelain in the tablet is 25 mg-75 mg. In one embodiment, the amount of stem bromelain in the tablet is 40 mg-60 mg. In one embodiment, the amount of stem bromelain in the tablet is 50 mg.

The present application provides an oral care composition comprising:
a) one or more omega fatty acids;
and one or more of the following:
b) one or more emulsifying agents;
c) one or more protease enzymes;
d) one or more soluble calcium phosphate remineralizing agents;
e) one or more whitening agents.

In one embodiment, the composition comprising:
a) one or more omega fatty acids;
and two or more of the following:
b) one or more emulsifying agents;
c) one or more protease enzymes;
d) one or more soluble calcium phosphate remineralizing agents;
e) one or more whitening agents.

In one embodiment, the composition comprising:
a) one or more omega fatty acids;
and three or more of the following:
b) one or more emulsifying agents;
c) one or more protease enzymes;
d) one or more soluble calcium phosphate remineralizing agents;
e) one or more whitening agents.

In one embodiment, the composition comprising each of the following:
a) one or more omega fatty acids;
b) one or more emulsifying agents;
c) one or more protease enzymes;
d) one or more soluble calcium phosphate remineralizing agents;
e) one or more whitening agents.

The present application provides an oral care composition comprising:
a) emu oil;
and one or more of the following:
b) one or more emulsifying agents;
c) one or more protease enzymes;
d) one or more soluble calcium phosphate remineralizing agents;
e) one or more amino acids.

In one embodiment, the composition comprising:
a) emu oil;
and two or more of the following:
b) one or more emulsifying agents;
c) one or more protease enzymes;
d) one or more soluble calcium phosphate remineralizing agents;
e) one or more amino acids.

In one embodiment, the composition comprising:
a) emu oil;
and three or more of the following:
b) one or more emulsifying agents;
c) one or more protease enzymes;
d) one or more soluble calcium phosphate remineralizing agents;
e) one or more amino acids.

In one embodiment, the composition comprising:
a) emu oil;
b) one or more emulsifying agents;
c) one or more protease enzymes;
d) one or more soluble calcium phosphate remineralizing agents;
e) one or more amino acids.

The present application also provides an oral care composition comprising:
a) one or more omega fatty acids;
and one or more of the following:
b) one or more emulsifying agents;
c) one or more protease enzymes;
d) one or more soluble calcium phosphate remineralizing agents;
e) one or more amino acids.

In one embodiment, the composition comprising:
a) one or more omega fatty acids;
and two or more of the following:
b) one or more emulsifying agents;
c) one or more protease enzymes;
d) one or more soluble calcium phosphate remineralizing agents;
e) one or more amino acids.

In one embodiment, the composition comprising:
a) one or more omega fatty acids;
and three or more of the following:
b) one or more emulsifying agents;
c) one or more protease enzymes;
d) one or more soluble calcium phosphate remineralizing agents;
e) one or more amino acids.

In one embodiment, the composition comprising:
a) one or more omega fatty acids;
b) one or more emulsifying agents;
c) one or more protease enzymes;
d) one or more soluble calcium phosphate remineralizing agents;
e) one or more amino acids.

In one embodiment, the composition wherein one or more of the protease enzymes are selected from the group consisting of stem bromelain, papain, trypsin, chymotrypsin, aminopeptidase, carboxypeptidase, pepsin, and cathepsin.

In one embodiment, the composition wherein the one or more amino acids are selected from the group consisting of arginine and glutamine.

In one embodiment, the composition wherein the one or more soluble calcium phosphate remineralizing agents are selected from the group consisting of dibasic calcium phosphate, monocalcium phosphate, tricalcium phosphate, and tetracalcium phosphate.

In one embodiment, the composition wherein the one or more emulsifying agents are phospholipids.

In one embodiment, the composition wherein at least one of the phospholipids is soy lecithin.

In one embodiment, the composition wherein the composition further comprises an isomalt.

In one embodiment, the composition wherein the isomalt is selected from the group consisting of galenIQ™ 720 and galenIQ™ 721.

In one embodiment, the composition wherein the composition further comprises a disintegrating agent.

In one embodiment, the composition wherein the disintegrating agent is crospovidone.

In one embodiment, the composition wherein the composition further comprises magnesium stearate.

In one embodiment, the composition wherein the composition further comprises glycerin.

In one embodiment, the composition wherein the composition further comprises fluoride.

In one embodiment, the composition wherein the remineralizing agent is white in color.

In one embodiment, the composition wherein the composition is formulated as a tablet, a bilayer tablet, a multilayer tablet, chewing gum, a toothpaste, a lozenge, a powder, a gel, a viscous gel, an ointment, a cream, a liquid, a mouthwash, or a candy.

In one embodiment, the composition wherein the composition is formulated as a tablet.

In one embodiment, the composition wherein the amino acids are present only in the coating of the tablet.

In one embodiment, the composition wherein the amino acids are present only in the outermost layer of the tablet.

In one embodiment, the composition is formulated as a bilayer tablet.

In one embodiment, the amino acids are present only in a single layer of the bilayer tablet In one embodiment, the composition comprises the amino acids in an amount between 0.01 to 25% by weight In one embodiment, the composition comprises the amino acids in en amount between 1 to 20% by weight In one embodiment, the composition comprises the amino acids in an amount of 10 to 15% by weight In one embodiment, the composition comprises the amino acids in an amount of 5 to 10% by weight In one embodiment, the composition comprises the amino acids in an amount of 1 to 5% by weight In one embodiment, the composition comprises the amino acids in an amount of 0.01 to 0.5% by weight In one embodiment, the composition wherein the emu oil is Black emu oil or Baramol emu oil.

In one embodiment, the composition wherein the composition comprises emu oil in an amount between 6 to 10% by weight.

In one embodiment, the composition wherein the composition comprises emu oil in an amount between 8 to 10% by weight.

In one embodiment, the composition wherein the composition comprises emu oil in an amount of 10% by weight.

In one embodiment, the composition wherein the composition comprises the one or more omega fatty acids in an amount between 6 to 10% by weight.

In one embodiment, the composition wherein the composition comprises the one or more omega fatty acids in an amount between 8 to 10% by weight.

In one embodiment, the composition wherein the composition comprises the one or more omega fatty acids in an amount of 10% by weight.

In one embodiment, the composition wherein the composition comprises the remineralizing agent in an amount between 5 to 10% by weight.

In one embodiment, the composition wherein the composition comprises the remineralizing agent in an amount of 10% by weight.

In one embodiment, the composition wherein the composition comprises the emulsifying agent in an amount between 1 to 5% or 1 to 10% by weight.

In one embodiment, the composition wherein the composition comprises the emulsifying agent in an amount between 2 to 4% by weight.

In one embodiment, the composition wherein the composition comprises the emulsifying agent in an amount of 10% by weight.

In one embodiment, the composition wherein the composition comprises the protease enzyme in an amount between 1 to 10% by weight.

In one embodiment, the composition wherein the composition comprises the protease enzyme in an amount between 5 to 10% by weight.

In one embodiment, the composition wherein the composition comprises the protease enzyme in an amount of 5% by weight.

In one embodiment, the composition further comprising a sweetener, colorant or flavoring agent.

In one embodiment, the composition further comprising polyethylene glycol. The polyethylene glycol provides improved texture and allows for better mixing of the fatty acids present in the composition. The polyethylene glycol provides improved hardness and texture wherein combined with other excipients including, but not limited to, isomalt.

In one embodiment, the composition is a micelle.

In one embodiment, the composition is a liposome.

In one embodiment, the composition is at least one of a micelle or liposome.

In one embodiment, the one or more proteases are encapsulated by or contained in the liposome.

In one embodiment, the one or more soluble calcium phosphate remineralizing agents are encapsulated by the liposome.

In one embodiment, the one or more amino acids are encapsulated by or contained in the liposome.

In one embodiment, the lipid bilayer of liposome comprises omega fatty acids.

In one embodiment, a method of delivering the one or more proteases to the oral cavity of a subject.

In one embodiment, a method of delivering the one or more proteases to the dentition of a subject.

In one embodiment, a method of delivering the one or more soluble calcium phosphate remineralizing agents to the oral cavity of a subject.

In one embodiment, a method of delivering the one or more soluble calcium phosphate remineralizing agents to the dentition of a subject.

In one embodiment, a method of delivering the one or more amino acids to the oral cavity of a subject.

In one embodiment, a method of delivering the one or more proteases to the oral cavity of a subject suffering from xerostomia or mucositis.

In one embodiment, a method of delivering the one or more soluble calcium phosphate remineralizing agents to the oral cavity of a subject suffering from xerostomia or mucositis.

In one embodiment, a method of delivering the one or more amino acids to the oral cavity of a subject suffering from xerostomia or mucositis.

In one embodiment, the composition comprising
a) 10% by weight emu oil;
b) 2% by weight one or more emulsifying agents;
c) 5% by weight one or more protease enzymes;
d) 5% by weight one or more soluble calcium phosphate remineralizing agents;
e) 10% by weight water; and
f) about 68% by weight polyethylene glycol.

In one embodiment, the composition comprising
a) 10% by weight black emu oil;
b) 2% by weight one or more emulsifying agents;
c) 5% by weight one or more protease enzymes;
d) 5% by weight one or more soluble calcium phosphate remineralizing agents;
e) 10% by weight water; and
f) about 68% by weight polyethylene glycol.

In one embodiment, the composition comprising
a) 10% by weight emu oil;
b) 2% by weight soy lecithin;
c) 5% by weight bromelain;
d) 5% by weight amorphous calcium phosphate;
e) 10% by weight water; and
f) about 68% by weight polyethylene glycol.

In one embodiment, the composition comprising
a) 10% by weight black emu oil;
b) 2% by weight soy lecithin;
c) 5% by weight bromelain;
d) 5% by weight amorphous calcium phosphate;
e) 10% by weight water; and
f) about 68% by weight polyethylene glycol.

In one embodiment, the composition comprising
a) about 10% by weight emu oil;
b) about 2% by weight one or more emulsifying agents;
c) about 5% by weight one or more protease enzymes;
d) about 5% by weight one or more soluble calcium phosphate remineralizing agents;
e) about 10% by weight water; and
f) about 68% by weight polyethylene glycol.

In one embodiment, the composition comprising
a) about 10% by weight black emu oil;
b) about 2% by weight one or more emulsifying agents;
c) about 5% by weight one or more protease enzymes;
d) about 5% by weight one or more soluble calcium phosphate remineralizing agents;
e) about 10% by weight water; and
f) about 68% by weight polyethylene glycol.

In one embodiment, the composition comprising
a) about 10% by weight emu oil;
b) about 2% by weight soy lecithin;
c) about 5% by weight bromelain;
d) about 5% by weight amorphous calcium phosphate;
e) about 10% by weight water; and
f) about 68% by weight polyethylene glycol.

In one embodiment, the composition comprising
a) about 10% by weight black emu oil;
b) about 2% by weight soy lecithin;
c) about 5% by weight bromelain;
d) about 5% by weight amorphous calcium phosphate;
e) about 10% by weight water; and
f) about 68% by weight polyethylene glycol.

The present application further provides a method of treating a subject suffering from xerostomia which comprises administering to the subject, in an amount effective to treat the xerostomia, a composition of the present application.

The present application further provides a method of treating a subject suffering from mucositis which comprises administering to the subject, in an amount effective to treat the mucositis, a composition of the present application.

In one embodiment, the method wherein the composition remineralizes teeth in the subject's mouth.

In one embodiment, the method wherein the composition reduces inflammation in the subject's mouth.

In one embodiment, the method wherein the composition lubricates the subject's mouth.

In one embodiment, the method wherein the composition reconditions the dental pellicle in the subject's mouth.

In one embodiment, the method wherein the composition provides a soothing effect in the subject's mouth.

In one embodiment, the method wherein the composition prevents caries the subject's mouth.

In one embodiment, the method wherein the subject is a human.

In one embodiment, the method wherein the subject has an autoimmune disease, diabetes, Sjögren's syndrome, or has recently undergone radiation therapy or chemotherapy.

In one embodiment, the method wherein the subject is concurrently taking one or more medications that causes xerostomia.

In one embodiment, any of the above compositions of the present application further comprising one or more amino acids.

In one embodiment, the one or more amino acids are included in the coating of the composition.

In one embodiment, the one or more amino acids are included in the outer layer of the composition.

In one embodiment, the composition is a bilayer table exemplified in FIG. 1 and the one or more amino acids are included in the upper layer of the tablet.

Figure 2:
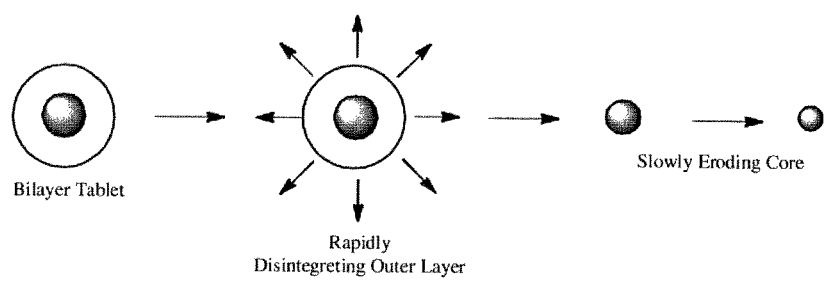
FIG. 2. Bilayer Tablet comprising a slowly eroding core and a rapidly disintegrating outer layer.

In one embodiment, the composition is a bilayer table exemplified in FIG. 2 and the one or more amino acids are included in the outer layer of the tablet.

In one embodiment, the composition comprising each of the following:
a) emu oil;
and one or more of the following:
b) one or more amino acids;
c) one or more protease enzymes; and
d) one or more soluble calcium phosphate remineralizing agents.

In one embodiment, the composition comprising each of the following:
   a) emu oil;
   and one or more of the following:
   b) one or more amino acids;
   c) one or more emulsifying agents;
   c) one or more protease enzymes; and
   d) one or more soluble calcium phosphate remineralizing agents.

In one embodiment, the composition wherein the one or more amino acids are glutamine or arginine.

In one embodiment, the composition wherein the one or more amino acids are L-glutamine or L-arginine.

In one embodiment, the emu oil is Baramol emu oil.

In one embodiment, the emu oil is Black emu oil.

In one embodiment, the composition wherein the one or more omega fatty acids comprise omega-3 fatty acids or omega-6 fatty acids.

In one embodiment, the composition wherein the omega-3 fatty acid is alpha-linoleic acid and the omega-6 fatty acid is gamma-linoleic acid.

In one embodiment, a composition for treating xerostomia. In one embodiment, a composition for treating dry mouth. In one embodiment, a composition for treating mucositis.

In some embodiments of the present methods, the mucositis is mucositis of the oral cavity and pharynx. In some embodiments of the present methods, the xerostomia is xerostomia of the oral cavity and pharynx.

In one embodiment, a composition for whitening teeth.

In one embodiment, a composition for remineralizing teeth.

In one embodiment, a composition for whitening and remineralizing teeth.

In one embodiment, the composition has a cariostatic effect on the subject's teeth. In one embodiment, the composition has an anti-cariogenic effect on the subject's teeth.

In one embodiment, the concentration of emu oil in the composition is between 0.1 to 60% by weight.

In one embodiment, the concentration of peroxide in the composition is between 0.1 to 50% by weight. Concentration of peroxide in excess of 40% by weight would be for professional use.

In one embodiment, the concentration of soluble calcium phosphate in the composition is between 0.1 to 50% by weight.

In one embodiment, the concentration of the protease enzyme in the composition is between 0.1 to 40% by weight.

In one embodiment, the concentration of the phospholipids in the composition is between 0.1 to 20% by weight.

In one embodiment, the concentration of emu oil in the slowly eroding layer is between 0.1 to 15% by weight. In one embodiment, the concentration of emu oil in the slowly eroding layer is between 1.0 to 10% by weight. In one embodiment, the concentration of emu oil in the slowly eroding layer is between 5 to 10% by weight. In one embodiment, the concentration of emu oil in the slowly eroding layer is 10% by weight.

In some embodiments, the whitening agent is an oxidizing agent.

Different oxidizing agent can be used in the composition. Examples of oxidizing agent include, but are not limited to peroxides. In some embodiments, the whitening agent is selected from the group comprising of one or more of carbamide peroxide and hydrogen peroxide.

In one embodiment, the concentration of the peroxide in the disintegrating layer is between 0.1 to 20% by weight. In one embodiment, the concentration of the peroxide in the disintegrating layer is between 1.0 to 20% by weight. In one embodiment, the concentration of the peroxide in the disintegrating layer is between 1.0 to 10% by weight. In one embodiment, the concentration of the peroxide in the disintegrating layer is between 1.0 to 5% by weight. In one embodiment, the concentration of the peroxide in the disintegrating layer is 1.0% by weight.

Different protease enzymes can be used in the composition. Examples of proteases include, but are not limited to, the group comprising of one or more of papain, trypsin, chymotrypsin, aminopeptidase, carboxypeptidase, pepsin, and cathepsin.

In one embodiment, papain is used. In one embodiment, the protease enzyme is obtained from a *papaya* extract.

In one embodiment, the concentration of the protease enzyme in the slow eroding layer is between 0.1% to 20% by weight. In one embodiment, the concentration of the protease enzyme in the slow eroding layer is between 1% to 20% by weight. In one embodiment, the concentration of the protease enzyme in the slow eroding layer is between 1% to 10% by weight. In one embodiment, the concentration of the protease enzyme in the slow eroding layer is between 5% to 15% by weight. In one embodiment, the concentration of the protease enzyme in the slow eroding layer is 5% by weight. In one embodiment, the concentration of the protease enzyme in the slow eroding layer is 10% by weight.

In one embodiment, the soluble calcium phosphate remineralizing agent is selected from the group comprising of one or more of dibasic calcium phosphate, monocalcium phosphate, dicalcium phosphate anhydrous, tricalcium phosphate, and tetracalcium phosphate. In one embodiment, tricalcium phosphate, dicalcium phosphate anhydrous, tetracalcium phosphate or dibasic calcium phosphate anhydrous are used. In one embodiment, tricalcium phosphate is used.

In one embodiment, the concentration of the soluble calcium phosphate remineralizing agent in the disintegrating layer is between 0.1% to 50% by weight. In one embodiment, the concentration of the soluble calcium phosphate remineralizing agent in the disintegrating layer is between 1% to 25% by weight. In one embodiment, the concentration of the soluble calcium phosphate remineralizing agent in the disintegrating layer is between 5% to 25% by weight. In one embodiment, the concentration of the soluble calcium phosphate remineralizing agent in the disintegrating layer is between 9.5% to 20% by weight.

In one embodiment, the concentration of the soluble calcium phosphate remineralizing agent in the disintegrating layer is 9.5% by weight. In one embodiment, the concentration of the soluble calcium phosphate remineralizing agent in the disintegrating layer is 20% by weight.

In one embodiment, the concentration of the soluble calcium phosphate remineralizing agent in the slowly eroding layer is between 0.1% to 50% by weight. In one embodiment, the concentration of the soluble calcium phosphate remineralizing agent in the slowly eroding layer is between 1% to 35% by weight. In one embodiment, the concentration of the soluble calcium phosphate remineralizing agent in the slowly eroding layer is between 10% to 35% by weight. In one embodiment, the concentration of the soluble calcium phosphate remineralizing agent in the slowly eroding layer is 10% by weight. In one embodiment, the concentration of the soluble calcium phosphate remineralizing agent in the slowly eroding layer is 35% by weight.

In one embodiment, the concentration of the phospholipids in the slow eroding layer is between 0.1% to 20% by weight. In one embodiment, the concentration of the phospholipids in the slow eroding layer is between 1% to 10% by weight. In one embodiment, the concentration of the phospholipids in the slow eroding layer is between 1% to 2% by weight. In one embodiment, the concentration of the phospholipids in the slow eroding layer is 2% by weight. In one embodiment, the concentration of the phospholipids in the slow eroding layer is 1% by weight.

In order for calcium phosphate to act as a remineralizing agent, it is preferable that the calcium phosphate be in soluble form. If a significant portion of the calcium phosphate were to precipitate out of solution, it would function as an abrasive agent and not as a remineralizer. The addition of glycerin to the composition acts to keep the calcium phosphate from forming a precipitate.

In one embodiment, the composition further comprises glycerin. In one embodiment, the concentration of glycerin is between 10 to 60% by weight.

In one embodiment, the composition further comprises fluoride, for example sodium fluoride. In one embodiment, the concentration of sodium fluoride is between 0.01 to 5% by weight. In yet another embodiment, the concentration of sodium fluoride is between 0.0001 to 5% by weight. In yet another embodiment, the amount of sodium fluoride is between 1 to 2 ppm.

In one embodiment, the remineralizing agent is white in color. Thus, the uptake of remineralizing material may contribute to the whitening effect.

In one embodiment, the composition contains potassium nitrate, which can act as a desensitizing agent.

The composition can be provided in a carrier. In different embodiments, the carrier is selected from the group consisting of a tablet, a bilayer tablet, a multilayer tablet, a chewing gum, a candy, a toothpaste, a lozenge, a powder, a gel, a viscous gel, an ointment, a cream, a liquid, a mouthwash, and a candy.

In one embodiment, the liquid carrier or mouthwash carrier further comprises sodium bicarbonate.

In some embodiments, the bilayer tablet comprises a disintegrating layer and a slowly eroding layer. The differing relative rates of release of active material content from the disintegrating layer and a slowly eroding layer of the tablet may be achieved in various ways.

The differing rates of release may be achieved by a first layer which is a disintegrating layer which releases the bulk of its active material content within a relatively short time, for example, including, but not limited to, within 1 min, 10 min, 30 min, or 1 hour, and a second layer which is a slowly eroding layer which releases the bulk of its active material content during a relatively long period after administration or after a period of delay after administration.

The disintegrating layer may have a composition similar to that of known rapidly disintegrating tablets. Slowly eroding layers may have a composition similar to that of known slowly eroding tablets and may comprise active material content together with a release retarding material.

In some embodiments, the composition is a single layer tablet comprising a disintegrating fraction and a slowly eroding fraction. The disintegrating fraction may be intermingled uniformly or randomly with the slowly eroding fraction. In some embodiments, the whitening agent is found only in the disintegrating fraction.

In some embodiments, the composition is a bilayer layer tablet comprising a slowly eroding tablet core and a disintegrating outer layer. In some embodiments, the whitening agent is found only in the disintegrating outer layer.

The advantages of the compositions disclosed herein include possible synergistic effects between the actions of the protease and the whitening agent, and ease of use especially in a home or veterinary setting. The compositions described in this patent disclosure are believed to provide improved effects both on extrinsic dental stains and on previously "untouchable" intrinsic dental stains. The removal of chromogen from enamel is believed to be aided by the presence in the composition of a protease enzyme able to react with protein chromogens and the pellicle layer, creating enhanced mechanisms for penetration of an oxygen free radical bleaching agent (e.g., hydrogen peroxide molecules from carbamide peroxide solution or hydrogen peroxide solution). It is believed that one of the effects of including proteases with whitening agents in accordance with this patent disclosure is deeper penetration of the whitening agents into enamel, in addition to the beneficial effect of the reaction of proteases with protein chromogens.

The composition provides an advantageous ease of use in that it allows for treatment of xerostomia and a whitening agent, a protease enzyme, and a remineralizing agent to be applied to teeth using only a single composition rather than having to apply the different components in separate compositions. This is particularly advantageous for home and veterinary use, and when the composition is supplied in certain carriers, such as for example chewing gum, toothpaste, lozenge, mouthwash, and candy.

The composition has the further advantage that when available application time is limited, the whitening agent, protease enzyme, and remineralizing agent can be simultaneously applied to the teeth for the full duration of the application time. In contrast, for the same total available treatment time, if the whitening agent, protease enzyme, and remineralizing agent were applied in separate compositions, the time of application of each component would have to be reduced in order to keep total treatment time constant.

In one embodiment of the composition, silica is added to the composition to increase the viscosity of the composition. In other embodiments, the composition contains methylcellulose (10-20% by weight) or xantahan gum (10-20% by weight).

In some embodiments, a sweetener or flavorant can be added to the composition. In one embodiment, the concentration is between about 0.2-10% by weight. In one embodiment the sweetener is saccharin or aspartame. In one embodiment the flavorant is peppermint or clove.

In some embodiments, the sweetener is maltitol, isomaltitol, manitol, lactitol, acesulfame potassium, cyclamate, taumatin or other known sweeteners. In some embodiments, the sweetener is sucralose or erythritol or a combination of both.

The pH of the composition can be adjusted. In one embodiment, the pH is between about pH 6 to 7.5. In one embodiment, baking soda is used as a pH neutralizer.

Advantageous methods for whitening and remineralizing teeth are also disclosed. The methods comprise applying to teeth any of the compositions described herein for whitening and remineralizing teeth.

In a further embodiment of any of the methods of whitening and remineralizing a subject's teeth described herein, a gel polymer is used at the base of the teeth to contain the whitening and remineralizing compositions to the teeth and to help avoid their contact with the gum. Soft gel polymers act as a barrier to the gingival sulcus and oral tissues. In different embodiments, the gel comprises polyethyl methylacrylate or polymethyl methylacrylate with plasticizers. A dental tray or dam can also be used for isolation of the dentition.

The total time for application of whitening and remineralization compositions can typically vary from 20-30 minutes to 2-3 hours. In a home application setting, compositions can be applied to the teeth overnight. In home application kits, the treatment time may vary between 1-2 weeks to up to several weeks depending upon the stain. In one embodiment, the whitening and remineralizing composition includes a light activated photo-initiator as an indicator of time exposure.

The compositions, kits and methods described herein can be used both on natural teeth and on some types of artificial teeth.

Using the compositions, kits and methods described herein, loss of calcium that may occur during dental bleaching can be restored by remineralization so that a more efficacious whitening composition can be used safely with enhanced effect.

Advantageous methods for treating dental sensitivity and for treating dental caries are also described herein and comprise applying any of the compositions described herein to the subject's teeth. Bleaching can cause dental sensitivity. This sensitivity can be treated using the described compositions, kits and methods for tooth whitening and remineralization. In addition, the described compositions, kits, and methods can be used to treat dental sensitivity that occurs in the absence of bleaching. Remineralization may decrease sensitivity by decreasing the permeability of dentin. In addition, the described compositions, kits and methods for tooth whitening and remineralization can be used in other applications where remineralization would be beneficial, for example in the treatment of dental caries.

After the whitening and remineralizing procedures described herein have been carried out, additional compositions for restorative or cosmetic purposes may be applied to the teeth.

As used herein, "treating" means preventing, slowing, halting, or reversing the progression of a condition, disease or infection. Treating may also mean improving one or more symptoms of a condition, disease or infection.

The compositions used in the method disclosed in this patent specification may be administered in various forms, including those detailed herein. The treatment with the compositions may be a component of a combination therapy or an adjunct therapy, i.e. the subject or patient in need of the composition is treated or given another drug or composition for the condition, disease or infection in conjunction with one or more of the instant compositions. This combination therapy can be sequential therapy where the patient is treated first with one composition or drug and then the other or the two are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compositions to the animal or human. The carrier may be liquid or solid and is selected with the planned manner of administration in mind. Liposomes are also a pharmaceutically acceptable carrier.

The dosage of the compositions administered in treatment will vary depending upon factors such as the pharmacodynamic characteristics of the compositions and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the composition used in the method of the present invention may comprise a single composition or mixtures thereof with additional agents. The compounds can be administered in oral dosage forms as tablets, capsules, pills, powders, granules, elixirs, tinctures, suspensions, syrups, and emulsions.

The compositions used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices.

The compositions can be administered alone or mixed with a pharmaceutically acceptable carrier. This carrier can be a solid or liquid, and the type of carrier is generally chosen based on the type of administration being used.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as *acacia*, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In the present application, all numbers or percentages disclosed herein are approximate values, regardless whether the word "about" or "approximate" is used in connection therewith. They may vary by 1 percent, 2 percent, 5 percent, or up to 20 percent. Whenever a numerical range with a lower limit and an upper limit is disclosed, any number falling within the range is specifically disclosed.

Each embodiment disclosed herein is contemplated as being applicable to each of the other disclosed embodiments. Thus, all combinations of the various elements described herein are within the scope of the invention.

This patent specification will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Materials and Methods

When possible, compendial (e.g, USP) grades or pharmaceutical grades of the chemicals were obtained. Carbamide peroxide is an oxidizing agent generally used for its oxygen-releasing effect in the local treatment and hygienic prevention of minor infections and inflammation or irritation of the gums and mouth, including canker sores (aphthous ulcers), gingivitis, periodontitis, stomatitis, and Vincent's infection. The drug also is used in the treatment of minor inflammation caused by dentures, mouth appliances (orthodontics), or dental procedures. The material obtained here is a white, crystalline powder with a relatively large particle size.

Omega fatty acids include omega-3 fatty acid, omega-6 fatty acid and omega-9 fatty acids. Omega-3 fatty acids are a family of unsaturated fatty acids that have in common a final carbon-carbon double bond in the n-3 position, that is, the third bond, counting from the methyl end. Omega-6 fatty acids are a family of unsaturated fatty acids that have in common a final carbon-carbon double bond in the n-6 position, that is, the sixth bond, counting from the methyl end. Omega-9 fatty acids are a family of unsaturated fatty acids that have in common a final carbon-carbon double bond in the n-9 position, that is, the ninth bond, counting from the methyl end.

Omega-3 fatty acids include but are not limited to Hexadecatrienoic acid (HTA), alpha-Linolenic acid (ALA), Stearidonic acid (SDA). Eicosatrienoic acid (ETE), Eicosatetraenoic acid (ETA), Eicosapentaenoic acid (EPA), Heneicosapentaenoic acid (HPA), Docosapentaenoic acid (DPA), Clupanodonic acid, Docosahexaenoic acid (DHA), Tetracosapentaenoic acid or Tetracosahexaenoic acid.

Omega-6 fatty acids include but are not limited to Gamma-linolenic acid (GLA), Calendic acid, Eicosadienoic acid, Dihomo-gamma-linolenic acid (DGLA), Arachidonic acid (AA), Docosadienoic acid, Adrenic acid, Docosapentaenoic acid, Tetracosatetraenoic acid, or Tetracosapentaenoic acid.

Omega-9 fatty acids include but are not limited to oleic acid, elaidic acid, gondoic acid, mead acid, erucic acid, nervonic acid.

Essential fatty acids cannot be synthesized by the human body and must be obtained from a dietary source. Because humans lack the required enzyme to introduce carbon-carbon double bonds at carbon atoms beyond the ninth carbon atom in unsaturated fatty acids (the ninth carbon atom from the omega end of the chain). Gamma-linoleic acid (an ω-6 fatty acid) and alpha-linolenic acid (an ω-3 fatty acid) are essential fatty acids that must be obtained by humans from a dietary source to ensure good wellness.

Non-limiting examples of suitable oil materials include oleic canola Oil (*Brassica campestris, B. napus, B. rapa*; characterized by having an oleic content greater than 70%, e.g., hi oleic canola oil, very high oleic canola oil, or partially hydrogenated canola oil), marula kernel oil (*Sclerocarya birrea*), palm oil (*Elaeis Guineensis* Oil), palm olein, palm stearin, palm superolein, pecan oil, pumpkin seed oil, oleic safflower oil (*Carthamus Tinctorius*; characterized by having an oleic content of greater than about 30% and omega-6 fatty acid content of less than about 50%, e.g., hi oleic safflower oil), sesame oil (*Sesamum indicum, S. oreintale*), soybean oil (*Glycine max*, e.g., hi oleic soybean, low linolenic soybean oil, partially hydrogenated), oleic sunflower oil (*Helianthus annus*; characterized by having an oleic content of greater than about 40%, e.g., mid oleic sunflower or high oleic sunflower oil), and mixtures thereof. Oleic canola oil, palm oil, sesame oil, hi oleic safflower oil, hi oleic soybean oil, mid oleic sunflower oil, and high oleic sunflower oil are common plant-bred derived oils and may be also be derived from non-genetically modified organisms (non-GMO). The above oils are commercially-available from a number of vendors.

Emu oil is oil rendered from the fat of the emu, a bird indigenous to Australia. Unadulterated emu oil can vary widely in color and viscosity, but is generally a yellow liquid composed of approximately 70% unsaturated fatty acids. The largest component is oleic acid, a mono-unsaturated omega-9 fatty acid. Emu oil also contains roughly 20% linoleic acid (omega-6 fatty acid) and 1-2% linolenic acid (omega-3 fatty acid). Emu oil is marketed and promoted as a dietary supplement with a wide variety of claimed health benefits. Commercial emu oil supplements are not standardized and vary widely in their potency. The Emu Oil used herein is marketed as Pro-Emu Oil from Progressive Emu Inc., PO Box 590088, Birmingham, Ala. 35259 and is a formulated product which includes some vitamin E.

Emu oil is oil rendered from the fat of the emu, a bird indigenous to Australia. Unadulterated emu oil can vary widely in color and viscosity, but is generally a yellow liquid composed of approximately 70% unsaturated fatty acids. The largest component is oleic acid, a mono-unsaturated omega-9 fatty acid. Emu oil also contains roughly 20% linoleic acid (an omega-6 fatty acid) and 1-2% linolenic acid (an omega-3 fatty acid). Emu oil is marketed and promoted as a dietary supplement with a wide variety of claimed health benefits. Commercial emu oil supplements are not standardized and vary widely in their potency. The Emu Oil used herein is marketed as Pro-Emu Oil from Progressive Emu Inc., PO Box 590088, Birmingham, Ala. 35259 and is a formulated product which includes some vitamin E.

Lecithins vary greatly in their physical form, from viscous semi-liquids to powders, depending upon the free fatty acid content. They may also vary in color from brown to light yellow, depending upon whether they are bleached or unbleached or on the degree of purity. When they are exposed to air, rapid oxidation occurs, also resulting in a dark yellow or brown color. The Lecithin utilized herein is a brown to light yellow wax-like material that may be difficult to distribute throughout a solid powder by traditional blending. It should be noted that Lecithin is incompatible with esterases owing to hydrolysis and it is also incompatible with oxidizing agents. Thus, the Lecithin should be separated from the carbamide peroxide.

In addition to other pharmaceutical excipients, Agglomerated isomalt was chosen as "filler" for the tablet formulations. Specifically, galenIQ™ 720 (low solubility) and galenIQ™ 721 (high solubility) are agglomerated spherical isomalts for direct compression applications. In general, these excipients are of non-animal origin, they have very low hygroscopicity, grades with different solubilities are available, they have excellent chemical stability, and are highly resistant against degradation by enzymes and acids, they are generally regarded as a non-toxic, non-allergic and non-irritant material, and they have a pleasant sugar-like, natural sweet taste profile. The higher solubility grade would be appropriate for a rapidly disintegrating layer, whereas the low solubility grade would be appropriate for a slowly eroding layer.

Papain is a white or grayish-white, slightly hygroscopic powder. Its potency varies according to process of preparation with the usual grade digesting ~35 times its weight of lean meat. Papain is incompatible with strong oxidizers and inactivated by oxidation. The papain used herein is designated as USP.

Example 1

The initial study (Table 1) focused on incorporation of the emu oil and lecithin into a solid dosage form (slow eroding tablet). Emu oil has a fairly high melting point and the material employed here appears as a free flowing semi-solid at room temperature.

TABLE 1

Initial formulation for a slow eroding tablet layer containing oil, surfactant and re-mineralizing agent.

| Item | Component | % by Weight In Blend | Weight per tablet (mg) | Actual Wt. per batch (g) |
| --- | --- | --- | --- | --- |
| 1 | Isomalt (galenIQ 720) | 80.9 | 202.4 | 7.1994 |
| 2 | Anhydrous Dibasic Calcium Phosphate (Anhydrous Emcompress, JRS Pharma) | 11.5 | 28.68 | 1.0202 |
| 3 | Emu Oil (Pro-Emu Oil, Progressive Emu) | 5.68 | 14.21 | 0.5054 |
| 4 | Lecithin NF (Spectrum) | 1.91 | 4.764 | 0.1695 |
|  | TOTAL | 100.0 | 250.0 (approx.) | 8.895 |

The following outcomes were obtained from this initial trial:
The powder mass accommodated the oil well; a very clean and dust free mixture was obtained.
Distribution of the lecithin was non-uniform, and subsequent processing efforts involve melting the lecithin and/or mixing it with the Emu Oil to produce a liquid form before combining it with powder.
The mixture compacted easily on a Carver Press to form strong tablets. The oil appeared to reduce die wall friction sufficiently to obviate the need for the addition of a lubricant.
When placed in water, the tablet erodes slowly—complete erosion occurred in approximately 5 minutes. During this time, the liquid becomes cloudy, presumably due to emulsification of the oil. The dicalcium phosphate appears as insoluble particles.
The tablet has a neutral taste; the Isomalt does not provide noticeable sweetness nor does it provide the endothermic cooling associated with a filler like sorbitol.

Procedure for preparation of composition described in Table 1:
1) Accurately weigh the Emu Oil (Item 3) into a disposable polyethylene weighing dish.
2) Accurately weigh the Isomalt (Item 1) into a disposable polyethylene weighing dish.
3) Take a portion of the Isomalt weighed in step 2 and transfer it into the dish containing the Emu Oil. Use a spatula to mix the powder with the oil. After mixing, transfer this mass to a glass mortar. Repeat this procedure using additional portions of Isomalt until all the Emu Oil has been absorbed onto powder. Transfer any remaining Isomalt into the glass mortar.
4) Accurately weigh the Anhydrous Dibasic Calcium Phosphate (item 2) into a disposable polyethylene weighing dish, and transfer this powder into the glass mortar containing the Isomalt and Emu Oil mixture.
5) Triturate the mixture in the mortar with a pestle to obtain a uniform blend.
6) Accurately weigh the Lecithin (Item 4) and transfer it to the mixture in the mortar.
7) Triturate the mixture in the mortar with a pestle to obtain a uniform blend.
8) Compress powder samples into tablets using a Carver press.

Example 2

A second, similar formulation was processed. Given the taste assessment described above, aspartame was included as a sweetener (Table 2). In terms of processing, in this case, the lecithin was added to Emu oil and the mixture was warmed in a microwave oven to obtain a liquid mixture. This mixture was then added to the blend of isomalt and anhydrous dicalcium phosphate.

TABLE 2

Modified formulation for a slow eroding tablet layer containing oil, surfactant and remineralizing agent.

| Item | Component | % by Weight In Blend | Weight per tablet (mg) | Actual Wt. per batch (g) |
| --- | --- | --- | --- | --- |
| 1 | Isomalt (galenIQ 720) | 82.0 | 207.50 | 8.3000 |
| 2 | Anhydrous Dibasic Calcium Phosphate (Anhydrous Emcompress, JRS Pharma) | 10.0 | 25.00 | 1.0000 |
| 3 | Emu Oil (Pro-Emu Oil, Progressive Emu) | 6.00 | 15.00 | 0.6000 |
| 4 | Lecithin NF (Spectrum) | 1.00 | 2.50 | 0.1000 |
| 5 | Aspartame (Equal, Merisant Co.) | 1.00 | 2.50 | 0.1000 |
|  | TOTAL | 100.0 | 252.5 | 10.144 |

Heating of the lecithin/Emu oil mixture was done by placing a beaker in the microwave oven and heating for 30 second intervals. After each interval, the mixture was stirred. Fragments of the lecithin continued to be present and a total of approximately 5 intervals was required; it appeared that the lecithin eventually melted and/or dissolved in the oil. It should be noted that in subsequent processing, heating for longer time intervals led to apparent decomposition of the lecithin.

Tablets were produced from this blend and they had similar physical attributes to those obtained previously. The addition of the aspartame produced a slight improvement in taste, but additional sweetener could be required.

Procedure for preparation of composition described in Table 2:
1) Accurately weigh the Lecithin (Item 4) into a 50 mL glass beaker.
2) Tare the beaker containing the Lecithin and accurately weigh the Emu Oil (item 3) into the beaker containing the Lecithin.

3) Accurately weigh the Anhydrous Dibasic Calcium Phosphate (Item 2) into a disposable polyethylene weighing dish.
4) Transfer the Anhydrous Dibasic Calcium Phosphate (Item 2) into a glass mortar. Triturate until a fine powder is obtained.
5) Accurately weigh the Isomalt (Item 1) into a disposable polyethylene weighing dish. Transfer the Isomalt to the mortar containing Anhydrous Dibasic Calcium Phosphate. Triturate to obtain a uniform blend and then transfer the blend to a weighing dish.
6) Place the beaker containing the lecithin and Emu Oil into the microwave oven and heat until the Lecithin melts. Use a spatula to mix the Lecithin with the oil.
7) Take a portion of the powder mixture obtained from 5 and transfer it into the beaker containing the Lecithin and Emu Oil mixture. Use a spatula to mix the powder with the oil. After mixing, transfer mass to a glass mortar. Repeat this procedure using additional portions of powder mixture until all the Lecithin and Emu oil has been absorbed onto powder. Transfer any remaining powder into the glass mortar.
8) Triturate the mixture in the mortar with a pestle to obtain a uniform blend.
9) Accurately weigh the Aspartame (Item 5) and transfer it to the mixture in the mortar. Triturate to form a uniform mixture.
10) Compress powder samples into tablets using a Carver Press.

Example 3

Presented in Table 3 is a bilayer tablet formulation. An initial formulation was developed for the rapidly disintegrating layer, built around the concept of using a directly compressible dicalcium phosphate carrier and also including crospovidone, a so-called "super" disintegrant. Dicalcium phosphate seemed to be a good choice because it is inorganic and therefore not incompatible with the strong oxidizer carbamide peroxide. Also, the rapid disintegration would release a substantial quantity of a re-mineralizing agent. Due to its incompatibility with strong oxidizers, papain was included in the slow eroding layer, and the isomalt was replaced with sorbitol.

The following outcomes were obtained from this trial:

The sorbitol, which has a larger particle size than the isomalt, did not accommodate the oil as well. The overall character of the blend for the slow eroding layer was more "oily".

Each individual blend compacted easily to form strong tablets, as did the combination of materials for the bilayer tablet.

When placed in water, the disintegrating layer does indeed disintegrate rapidly releasing insoluble dicalcium phosphate particles.

The second layer erodes slowly.

The sorbitol did not produce an improvement in taste.

Procedure for preparation of composition described in Table 3:

Disintegrating Layer

1) Accurately weigh the Anhydrous Dibasic Calcium Phosphate (Item 2) into a disposable polyethylene weighing dish.
2) Accurately weigh the Carbamide Peroxide (Item 1) and transfer the powder into a glass mortar.
3) Geometrically add the Anhydrous Dibasic Calcium Phosphate into a glass mortar with trituration after each addition to produce a uniform blend.
4) Accurately weigh the Crospovidone (Item 3) and add it to the powder blend in the glass mortar. Triturate to form a uniform blend.
5) Accurately weigh the Magnesium Stearate (Item 4) and add it to the powder blend in the glass mortal. Triturate lightly to form a uniform blend.
6) Transfer the blend into a bulk container and hold for tableting.

Slow Eroding Layer

7) Accurately weigh the Lecithin (Item 9) into a 50 mL glass beaker.
8) Tare the beaker containing the lecithin and accurately weigh the Emu Oil (Item 8) into the beaker containing the Lecithin.
9) Accurately weigh the Anhydrous Dibasic Calcium Phosphate (Item 6) into a disposable polyethylene weighing dish.
10) Transfer the Anhydrous Dibasic Calcium Phosphate (item 6) into a glass mortar. Triturate until a fine powder is obtained,

TABLE 3

Initial Bilayer Tablet Formulation.

| Item | Component | % by Weight In Blend | Weight per tablet (mg) | Actual Wt. per batch (g) |
|---|---|---|---|---|
| | Disintegrating Layer | | | |
| 1 | Carbamide Peroxide (Spectrum) | 1.0 | 2.5 | 0.1018 |
| 2 | Anhydrous Dibasic Calcium Phosphate (Anhydrous Emcompress, JRS Pharma) | 94.5 | 236.3 | 9.508 |
| 3 | Crospovidone | 3.50 | 8.75 | 0.3528 |
| 4 | Magnesium Stearate | 1.00 | 2.5 | 0.1040 |
| | TOTAL | 100.0 | 250 | 10.0666 |
| | Slow Eroding Layer | | | |
| 5 | Sorbitol | 78.0 | 390.0 | 7.7701 |
| 6 | Anhydrous Dibasic Calcium Phosphate (Anhydrous Emcompress, JRS Pharma) | 10.0 | 50.00 | 1.0565 |
| 7 | Papain USP30 (Anhui) | 5.0 | 25.00 | 0.5664 |
| 8 | Emu Oil (Pro-Emu Oil, Progressive Emu) | 6.00 | 30.00 | 0.6488 |
| 9 | Lecithin NF (Spectrum) | 1.00 | 5.00 | 0.1399 |
| | TOTAL | 100 | 500.00 | 10.1817 |

11) Accurately weigh the Sorbitol (Item 5) into a disposable polyethylene weighing dish, Transfer the Sorbitol to the mortar containing the Anhydrous Dibasic Calcium Phosphate. Triturate to obtain a uniform blend and then transfer the blend to a weighing dish.

12) Place the beaker containing the Lecithin and Emu Oil into the microwave oven and heat until the Lecithin melts, Use a spatula to mix the Lecithin with the oil.

13) Take a portion of the powder mixture obtained from step 1 and transfer it into the beaker containing the Lecithin and Emu Oil mixture. Use a spatula to mix the powder with the oil. After mixing, transfer this mass to a glass mortar. Repeat this procedure using additional portions of powder mixture until all the Lecithin and Emu Oil has been absorbed onto powder. Transfer any remaining powder into the glass mortar.

14) Triturate the mixture in the mortar with a pestle to obtain a uniform blend.

15) Accurately weigh the Papain (Item 7) and add it into a glass mortar. Triturate until a uniform mixture is obtained.

16) Transfer the blend into a bulk container and hold for tableting.

Bilayer Tablet Production

17) Weigh approximately 500 mg of the powder for the slow eroding layer and transfer it into the die, Compress the powder into the first layer using a Carver Press.

18) Weigh approximately 250 mg of the powder for the disintegrating layer and transfer it into the die containing the first layer. Compress the powder onto the first layer using the Carver press.

19) Eject tablet from die.

Example 4

Modifications made in the next iteration (Table 4) include a replacement of the sorbitol with isomalt, and the use of relatively large, capsule-shaped tablet tooling. A tablet size of 1.2 g was targeted, with 400 mg and 800 mg for the disintegrating and eroding layers, respectively.

Subsequent to manufacture of these bilayer tablets, two things became evident. When handling this tablet, it appeared that the edges of this layer were easily abraded. Second, when placed in simulated intestinal fluid, a large quantity of insoluble dicalcium phosphate was released, which might be "gritty" and not be desirable.

Procedure for preparation of composition described in Table 4:

Disintegrating Layer

1) Accurately weigh the Anhydrous Dibasic Calcium Phosphate (Item 2) into a disposable polyethylene weighing dish, 2) Accurately weigh the Carbamide Peroxide (Item 1) and transfer the powder into a glass mortar, 3) Geometrically add the Anhydrous Dibasic Calcium Phosphate into a glass mortar with trituration after each addition to produce a uniform blend.

4) Accurately weigh the Crospovidone (Item 3) and add it to the powder blend in the glass mortar. Triturate to form a uniform blend.

5) Accurately weigh the Magnesium Stearate (Item 4) and add it to the powder blend in the glass mortal. Triturate lightly to form a uniform blend.

6) Transfer the blend into a bulk container and hold for tableting.

Slow Eroding Layer

7) Accurately weigh the Lecithin (Item 9) into a 50 mL glass beaker.

8) Tare the beaker containing the lecithin and accurately weigh the Emu Oil (Item 8) into the beaker containing the Lecithin.

9) Accurately weigh the Anhydrous Dibasic Calcium Phosphate (Item 6) into a disposable polyethylene weighing dish.

10) Transfer the Anhydrous Dibasic Calcium Phosphate (item 6) into a glass mortar. Triturate until a fine powder is obtained.

11) Accurately weigh the Isomalt (Item 5) into a disposable polyethylene weighing dish. Transfer the Isomalt to the mortar containing the Anhydrous Dibasic Calcium Phosphate. Triturate to obtain a uniform blend and then transfer the blend to a weighing dish.

TABLE 4

Carbamide Peroxide (4 mg) and Papain (40 mg) bilayer tablet formulation.

| Item | Component | % by Weight In Blend | Weight per tablet (mg) | Actual Wt. per batch (g) |
|---|---|---|---|---|
| | Disintegrating Layer | | | |
| 1 | Carbamide Peroxide (Spectrum) | 1.0 | 4.00 | 0.1107 |
| 2 | Anhydrous Dibasic Calcium Phosphate (Anhydrous Emcompress, JRS Pharma) | 94.5 | 378.00 | 9.479 |
| 3 | Crospovidone | 3.50 | 14.00 | 0.3601 |
| 4 | Magnesium Stearate | 1.00 | 4.00 | 0.1053 |
| | TOTAL | 100.0 | 400.0 | 10.0551 |
| | Slow Eroding Layer | | | |
| 5 | Isomalt | 78.0 | 624.0 | 7.7967 |
| 6 | Anhydrous Dibasic Calcium Phosphate (Anhydrous Emcompress, JRS Pharma) | 10.0 | 80.0 | 1.0722 |
| 7 | Papain USP30 (Anhui) | 5.0 | 40.0 | 0.5243 |
| 8 | Emu Oil (Pro-Emu Oil, Progressive Emu) | 6.00 | 48.0 | 0.6330 |
| 9 | Lecithin NF (Spectrum) | 1.00 | 8.0 | 0.1008 |
| | TOTAL | 100.0 | 800.0 | 10.127 |

12) Place the beaker containing the Lecithin and Emu Oil into the microwave oven and heat until the Lecithin melts, Use a spatula to mix the Lecithin with the oil.
13) Take a portion of the powder mixture obtained from step 11 and transfer it into the beaker containing the Lecithin and Emu Oil mixture. Use a spatula to mix the powder with the oil. After mixing, transfer this mass to a glass mortar. Repeat this procedure using additional portions of powder mixture until all the Lecithin and Emu Oil has been absorbed onto powder. Transfer any remaining powder into the glass mortar.
14) Triturate the mixture in the mortar with a pestle to obtain a uniform blend.
15) Accurately weigh the Papain (Item 7) and add it into a glass mortar. Triturate until a uniform mixture is obtained.
16) Transfer the blend into a bulk container and hold for tableting.

Bilayer Tablet Production

17) Weigh approximately 650 mg of the powder for the slow eroding layer and transfer it into the die, Compress the powder into the first layer using a Carver Press.
18) Weigh approximately 350 mg of the powder for the disintegrating layer and transfer it into the die containing the first layer. Compress the powder onto the first layer using the Carver press.
19) Eject tablet from die.

Example 5

A reduction in the quantity of phosphate salt was made and a soluble filler was added. Thus, in the next iteration (Table 5) the concentration of dicalcium phosphate was reduced and isomalt was included as the soluble filler in the disintegrating layer. The bilayer tablet produced from the formulation in Table 5 showed no signs of incompatibility in the dosage form. There is considerable flexibility in the tablet in terms of both composition, weight, and the weight of the respective layers.

Disintegrating Layer

1) Accurately weigh the Anhydrous Dibasic Calcium Phosphate (Item 2) into a disposable polyethylene weighing dish.
2) Accurately weigh the Carbamide Peroxide (Item 1) and transfer the powder into a glass mortar.
3) Add the Anhydrous Dibasic Calcium Phosphate into the glass mortar and triturate to produce a uniform blend.
4) Accurately weigh the Isomalt (Item 3) and add it to the powder blend in the glass mortar. Triturate to form a uniform blend.
5) Accurately weigh the Crospovidone (Item 4) and the Magnesium Stearate (Item 5) and add them to the powder blend in the glass mortar. Triturate lightly to form a uniform blend.
6) Transfer the blend into a bulk container and hold for tableting.

Slow Eroding Layer

7) Accurately weigh the Lecithin (Item 10) into a 50 mL glass beaker.
8) Tare the beaker containing the lecithin and accurately weigh the Emu Oil (Item 9) into the beaker containing the Lecithin.
9) Accurately weigh the Anhydrous Dibasic Calcium Phosphate (Item 6) into a disposable polyethylene weighing dish.
10) Transfer the Anhydrous Dibasic Calcium Phosphate (Item 7) into a glass mortar. Triturate until a fine powder is obtained,
11) Accurately weigh the Isomalt (Item 6) into a disposable polyethylene weighing dish. Transfer the Isomalt to the mortar containing the Anhydrous Dibasic Calcium Phosphate. Triturate to obtain a uniform blend and then transfer the blend to a weighing dish.
12) Place the beaker containing the Lecithin and Emu Oil into the microwave oven and heat until the Lecithin melts. Use a spatula to mix the Lecithin with the oil.
13) Take a portion of the powder mixture obtained from step 11 and transfer it into the beaker containing the Lecithin and

TABLE 5

Modified Carbamide Peroxide (4 mg) and papain (40 mg) bilayer tablet formulation.

| Item | Component | % by Weight In Blend | Weight per tablet (mg) | Actual Wt. per batch (g) |
|---|---|---|---|---|
| | Disintegrating Layer | | | |
| 1 | Carbamide Peroxide (Spectrum) | 1.0 | 4.00 | 0.1042 |
| 2 | Anhydrous Dibasic Calcium Phosphate (Anhydrous Emcompress, JRS Pharma) | 9.5 | 38.00 | 0.969 |
| 3 | Isomalt (galenIQ 720) | 85.0 | 340.00 | 8.519 |
| 4 | Crospovidone | 3.5 | 14.00 | 0.3488 |
| 5 | Magnesium Stearate | 1.00 | 4.00 | 0.1087 |
| | TOTAL | 100.0 | 400.0 | 10.0497 |
| | Slow Eroding Layer | | | |
| 6 | Isomalt (galenIQ 720) | 78.0 | 624.0 | 7.8036 |
| 7 | Anhydrous Dibasic Calcium Phosphate (Anhydrous Emcompress, JRS Pharma) | 10.0 | 80.0 | 1.406 |
| 8 | Papain USP30 (Anhui) | 5.0 | 40.0 | 0.5454 |
| 9 | Emu Oil (Pro-Emu Oil, Progressive Emu) | 6.00 | 48.0 | 0.6929 |
| 10 | Lecithin NF (Spectrum) | 1.00 | 8.0 | 0.1100 |
| | TOTAL | 100.0 | 800.0 | 10.1925 |

Procedure for preparation of composition described in Table 5:

Emu Oil mixture. Use a spatula to mix the powder with the oil. After mixing, transfer this mass to a glass mortar. Repeat this procedure using additional portions of powder mixture until all the Lecithin and Emu Oil has been absorbed onto powder. Transfer any remaining powder into the glass mortar.

14) Triturate the mixture in the mortar with a pestle to obtain a uniform blend.

15) Accurately weigh the Papain (Item 8) and add it into a glass mortar. Triturate until a uniform mixture is obtained.

16) Transfer the blend into a bulk container and hold for tableting.

Bilayer Tablet Production

17) Weigh approximately 800 mg of the powder for the slow eroding layer and transfer it into the die, Compress the powder into the first layer using a Carver Press.

18) Weigh approximately 400 mg of the powder for the disintegrating layer and transfer it into the die containing the first layer. Compress the powder onto the first layer using the Carver press.

19) Eject tablet from die.

Example 6

Presented in FIG. 7 is another formulation. Several changes were made including: 1) the weight of the rapidly disintegrating layer was reduced and that of the slowly eroding layer increased—there is no need for much mass to accommodate the carbamide peroxide, and the larger the mass of the slowly eroding layer the more oil can be included; 2) Emu oil level was increased to 10% and lecithin level was increased from 1% to 2%.

The Emu oil and lecithin were combined in a beaker and heated on a hot plate with stirring. The temperature required to "melt" the lecithin and incorporate it into the oil was quite high. While it is possible to obtain what appears to be a one phase solution of the two components, excessive heating may change the character of the oil and/or degrade the lecithin.

completely disperse. After compression, there were yellow spots on the tablet surface that indicated that the distribution of the Lecithin was not uniform. The mixture of the oil, lecithin, and powders may need to be heated to obtain the desired uniformity. In terms of larger scale production this can be accomplished in a jacketed high shear mixer. It appeared that more oil could be accommodated and the consistency of the slow eroding layer appears to be fine.

Procedure for preparation of composition described in Table 6:

Disintegrating Layer

1) Accurately weigh the Tricalcium Phosphate (Item 2) into a disposable polyethylene weighing dish.

2) Accurately weigh the Carbamide Peroxide (Item 1) and transfer the powder into a glass mortar.

3) Add the Tricalcium Phosphate into the glass mortar and triturate to produce a uniform blend.

4) Accurately weigh the Isomalt (Item 3) and add it to the powder blend in the glass mortar. Triturate to form a uniform blend.

5) Accurately weigh the Crospovidone (Item 4) and the Magnesium Stearate (Item 5) and add them to the powder blend in the glass mortar. Triturate lightly to form a uniform blend.

6) Transfer the blend into a bulk container and hold for tableting.

Slow Eroding Layer

7) Accurately weigh the Lecithin (Item 10) into a 50 mL glass beaker.

8) Tare the beaker containing the lecithin and accurately weigh the Emu Oil (Item 9) into the beaker containing the Lecithin.

9) Accurately weigh the Tricalcium Phosphate (Item 7) into a disposable polyethylene weighing dish.

10) Accurately weigh the Isomalt (Item 6) into a disposable polyethylene weighing dish.

TABLE 6

Modified Carbamide Peroxide (2 mg) and papain (100 mg) bilayer tablet formulation including tricalcium phosphate.

| Item | Component | % by Weight In Blend | Weight per tablet (mg) | Actual Wt. per batch (g) |
|---|---|---|---|---|
| | Disintegrating Layer | | | |
| 1 | Carbamide Peroxide (Spectrum) | 1.0 | 2.00 | 0.2185 |
| 2 | Tricalcium Phosphate, Powder NF | 20.0 | 40.00 | 3.995 |
| 3 | Isomalt (galenIQ 720) | 73.0 | 146.00 | 14.605 |
| 4 | Crospovidone | 4.00 | 8.00 | 0.8164 |
| 5 | Magnesium Stearate | 2.00 | 4.00 | 0.3880 |
| | TOTAL | 100.0 | 200.0 | 20.0229 |
| | Slow Eroding Layer | | | |
| 6 | Isomalt (galenIQ 720) | 43.0 | 430.0 | 8.5481 |
| 7 | Tricalcium Phosphate, Powder NF | 35.0 | 350.0 | 7.0121 |
| 8 | Papain USP30 (Anhui) | 10.0 | 100.0 | 2.0847 |
| 9 | Emu Oil (Pro-Emu Oil, Progressive Emu) | 10.0 | 100.0 | 2.0679 |
| 10 | Lecithin NF (Spectrum) | 2.00 | 20.0 | 0.4002 |
| | TOTAL | 100.0 | 1000.0 | 20.1130 |

The warm oily solution was added to the tricalcium phosphate with the expectation that it could be distributed uniformly throughout this powder. The combination of the fine powder and the decrease in temperature resulted in the formation of wax-like aggregates which were very hard to 11) Place the beaker containing the Lecithin and Emu Oil on a hot plate and heat until the Lecithin mixes with the oil.

12) Add the tricalcium phosphate from step 9 into the beaker containing the Lecithin and Emu Oil mixture. Use a spatula to mix the powder with the oil. After mixing, transfer the mass to a glass mortar. Repeat procedure using additional portions of the Isomalt powder from step 10 and continue until all the Lecithin and Emu Oil has been absorbed onto the powder. Transfer any remaining Isomalt powder into the glass mortar.
13) Triturate the mixture in the mortar with a pestle to obtain a uniform blend.
14) Accurately weigh the Papain (Item 8) and add it into a glass mortar. Triturate until a uniform mixture is obtained.
15) Transfer the blend into a bulk container and hold for tableting.

Bilayer Tablet Production
16) Weigh approximately 1000 mg of the powder for the slow eroding layer and transfer it into the die, Compress the powder into the first layer using a Carver Press.
17) Weigh approximately 200 mg of the powder for the disintegrating layer and transfer it into the die containing the first layer. Compress the powder onto the first layer using the Carver press.
18) Eject tablet from die.

Example 7

An attempt at increasing the oil level to 15% by weight is represented by the tablet described in Table 7. This batch was prepared at the 100 g size with the expectation that it could be compressed on an instrumented single station press to evaluate flow. However, when a screening study was done on the Carver press, the rapidly disintegrating layer did not adhere to the slowly eroding layer. The applied pressure essentially squeezed the oil out of the carrier producing a highly lubricated interface between the layers.

4) Accurately weigh the Isomalt (Item 3) and add it to the powder blend in the glass mortar. Triturate to form a uniform blend.
5) Accurately weigh the Crospovidone (Item 4) and the Magnesium Stearate (Item 5) and add them to the powder blend in the glass mortar. Triturate lightly to form a uniform blend.
6) Transfer the blend into a bulk container and hold for tableting.

Slow Eroding Layer
7) Accurately weigh the Lecithin (Item 10) into a glass beaker.
8) Tare the beaker containing the lecithin and accurately weigh the Emu Oil (Item 9) into the beaker containing the Lecithin.
9) Accurately weigh the Tricalcium Phosphate (Item 7) into a disposable polyethylene weighing dish.
10) Accurately weigh the Isomalt (Item 6) into a disposable polyethylene weighing dish.
11) Place the beaker containing the Lecithin and Emu Oil on a hot plate and heat until the Lecithin mixes with the oil.
12) Add the tricalcium phosphate from step 9 into the beaker containing the Lecithin and Emu Oil mixture. Use a spatula to mix the powder with the oil. After mixing, transfer the mass to a glass mortar. Repeat procedure using additional portions of the Isomalt powder from step 10 and continue until all the Lecithin and Emu Oil has been absorbed onto the powder. Transfer any remaining Isomalt powder into the glass mortar.
13) Triturate the mixture in the mortar with a pestle to obtain a uniform blend.

TABLE 7

Modified Carbamide Peroxide (2 mg) and papain (100 mg) bilayer tablet formulation including 15% emu oil.

| Item | Component | % by Weight In Blend | Weight per tablet (mg) | Actual Wt. per batch (g) |
|---|---|---|---|---|
| | Disintegrating Layer | | | |
| 1 | Carbamide Peroxide (Spectrum) | 1.0 | 2.00 | 1.0385 |
| 2 | Tricalcium Phosphate, Powder NF | 20.0 | 40.00 | 20.090 |
| 3 | Isomalt (galenIQ 720) | 73.0 | 146.00 | 73.068 |
| 4 | Crospovidone | 4.00 | 8.00 | 3.9924 |
| 5 | Magnesium Stearate | 2.00 | 4.00 | 2.0100 |
| | TOTAL | 100.0 | 200.0 | 100.1989 |
| | Slow Eroding Layer | | | |
| 6 | Isomalt (galenIQ 720) | 38.0 | 380.0 | 37.9956 |
| 7 | Tricalcium Phosphate, Powder NF | 35.0 | 350.0 | 35.0067 |
| 8 | Papain USP30 (Anhui) | 10.0 | 100.0 | 10.0530 |
| 9 | Emu Oil (Pro-Emu Oil, Progressive Emu) | 15.00 | 150.0 | 15.1024 |
| 10 | Lecithin NF (Spectrum) | 2.00 | 20.00 | 2.0863 |
| | TOTAL | 100.0 | 1000.0 | 100.244 |

Procedure for preparation of composition described in Table 7:

Disintegrating Layer
1) Accurately weigh the Tricalcium Phosphate (Item 2) into a disposable polyethylene weighing dish.
2) Accurately weigh the Carbamide Peroxide (Item 1) and transfer the powder into a glass mortar.
3) Add the Tricalcium Phosphate into the glass mortar and triturate to produce a uniform blend.

14) Accurately weigh the Papain (Item 8) and add it into a glass mortar. Triturate until a uniform mixture is obtained.
15) Transfer the blend into a bulk container and hold for tableting.

Bilayer Tablet Production
16) Weigh approximately 1000 mg of the powder for the slow eroding layer and transfer it into the die, Compress the powder into the first layer using a Carver Press.

17) Weigh approximately 200 mg of the powder for the disintegrating layer and transfer it into the die containing the first layer. Compress the powder onto the first layer using the Carver press.
18) Eject tablet from die.

Example 8

Tablet Formulation in Absence Peroxide

Ingredients:

| | |
|---|---|
| Spectrum Dicalcium Pyrophosphate Anhydrous (amorphous calcium phosphate) (DCP) | 5% |
| Black emu oil | 10% |
| Bromelain | 5% |
| Soy Lecithin (granulated) | 2% |
| Water (used to dissolve lecithin) | 10% |

Base
Polyethylene glycol (PEG) 3350 QS or Polyethylene glycol (PEG) 3350 QS and Isomalt 68%
Additional Ingredients
Sweeteners (0.05%) including, but not limited to, xylitol or sorbitol. Colouring or Flavouring including, but not limited to, sunset orange colour or pineapple flavour Procedure for preparation of composition described above:
1. Add water and lecithin together, leave for 2 hours or until lecithin dissolves at room temperature (18-21° C.) until homogenous.
2. Add emu oil, stir until emulsified, at room temperature (18-21° C.).
3. Weigh and add Bromelain, DCP, stir gently until homogenised at room temperature (18-21° C.)
4. Add colour, flavour, sweetener, stir until homogenised at room temperature (18-21° C.)
5. In same beaker add PEG.
6. Heat solution for PEG separately to melt but keep below 60° C., stir to evenly heat and maintain stirring to stop any point heat build-up, preferably holding temperature at 20-30° C.
7. Once fully melted stir PEG through till homogenised.
8. Whilst still liquid add mixed ingredients to moulds, if mixture becomes too stiff to pour then reheat, note to always keep mixture temperature below 60° C. as bromelain denatures above this temperature.

A above tablet is also formed further comprising one or more amino acids in an amount between 0.01 to 25% by weight (in place of the corresponding amount of one or more components, in particular in place of the corresponding amount of the base).

A above tablet is also formed further comprising one or more amino acids in an amount between 1 to 20% by weight (in place of the corresponding amount of one or more components, in particular in place of the corresponding amount of the base).

A above tablet is also formed further comprising one or more amino acids in an amount between 10 to 15% by weight (in place of the corresponding amount of one or more components, in particular in place of the corresponding amount of the base).

A above tablet is also formed further comprising one or more amino acids in an amount between 5 to 10% by weight (in place of the corresponding amount of one or more components, in particular in place of the corresponding amount of the base).

A above tablet is also formed further comprising one or more amino acids in an amount between 1 to 5% by weight (in place of the corresponding amount of one or more components, in particular in place of the corresponding amount of the base).

A above tablet is also formed further comprising one or more amino acids in an amount between 0.01 to 0.5% by weight (in place of the corresponding amount of one or more components, in particular in place of the corresponding amount of the base).

Example 9

The following compositions are prepared using the methods described hereinabove:
A composition comprising emu oil and one or more emulsifying agents.
A composition comprising omega fatty acids and one or more emulsifying agents. A composition comprising omega fatty acids and one or more protease enzymes. A composition comprising omega fatty acids and one or more soluble calcium phosphate remineralizing agents. A composition comprising omega fatty acids and one or more whitening agents. A composition comprising omega fatty acids and two of the following: one or more emulsifying agents, one or more protease enzymes, one or more soluble calcium phosphate remineralizing agents, one or more whitening agents. A composition comprising omega fatty acids and three of the following: one or more emulsifying agents, one or more protease enzymes, one or more soluble calcium phosphate remineralizing agents, one or more whitening agents. A composition comprising omega fatty acids, one or more emulsifying agents, one or more protease enzymes, one or more soluble calcium phosphate remineralizing agents, and one or more whitening agents.

A composition comprising emu oil and one or more emulsifying agents. A composition comprising emu oil and one or more protease enzymes. A composition comprising emu oil and one or more soluble calcium phosphate remineralizing agents. A composition comprising emu oil and one or more whitening agents. A composition comprising emu oil and two of the following: one or more emulsifying agents, one or more protease enzymes, one or more soluble calcium phosphate remineralizing agents, one or more whitening agents. A composition comprising emu oil and three of the following: one or more emulsifying agents, one or more protease enzymes, one or more soluble calcium phosphate remineralizing agents, one or more whitening agents. A composition comprising emu oil, one or more emulsifying agents, one or more protease enzymes, one or more soluble calcium phosphate remineralizing agents, and one or more whitening agents.

The above compositions are formulated as single layer tablets, bilayer tablets or as any one of the formulations described hereinabove.

Example 10

The composition of the present application is administered to a subject or subjects suffering from xerostomia and/or hyposalivation. The composition increases salivary flow in the subject(s). The composition also reduces the subjective sensation of dry mouth in the subject(s). The composition of the present application is administered to a subject's teeth. The composition whitens the subject's teeth.

The bilayer tablet composition of the present application comprising one or more whitening agents in the rapidly disintegrating layer and emu oil is administered to a subject or subjects suffering from xerostomia and/or hyposalivation. The bilayer tablet composition increases salivary flow in the subject(s). The composition also reduces the subjective sensation of dry mouth in the subject(s). The bilayer tablet composition of the present application comprising one or more whitening agents in the rapidly disintegrating layer and emu oil is administered to a subject's teeth. The bilayer tablet whitens the subject's teeth.

The bilayer tablet composition of the present application comprising one or more whitening agents in the rapidly disintegrating layer is administered to a subject's teeth. The bilayer tablet whitens the subject's teeth.

Example 11

A single first oral care composition of the present application followed by five second oral care compositions of the present application are administered over 24 hours to a subject suffering from xerostomia of the oral cavity and pharynx. The composition increases salivary flow in the subject(s). The composition also reduces the subjective sensation of dry mouth in the subject(s).

A single first oral care composition of the present application followed by five second oral care compositions of the present application are administered over 24 hours to a subject suffering from mucositis of the oral cavity and pharynx. The compositions treat the subject suffering from mucositis of the oral cavity and pharynx.

Example 12

An oral care composition of the present application further comprising one or more amino acids provides improved cellular repair, improved breakdown of mucus and improved anti-inflammatory response in the subject. In particular, the one or more amino acids decrease mucous membrane injury in subjects being treated with radiation therapy. Glutamine, in particular, acts as an antioxidant and/or antagonist of prostaglandin E2 when metabolized to glutathione.

The one or more amino acids, preferably arginine or glutamine, when combined with stem bromelain, emu oil, and amorphous calcium phosphate in a single oral care composition: (i) reduces mucinous proteins in the subject, (ii) decreases the risk of caries in the subject, (iii) decreases inflammation in the subject, (iv) improves cellular repair, and (v) coats the mouth of the subject to provide comfort to the subject.

For the reason stated above, the oral care composition of the present application further containing one or more amino acids provides improved treatment of xerostomia and mucositis in subjects afflicted therewith.

DISCUSSION

The composition disclosed herein relate to a stable, multi-component, solid dosage form for use in dental therapy that delivers an effective combination of emu oil, a whitening/cleansing agent, a protease enzyme, a re-mineralizing agent, and an emulsifying agent in the oral cavity. The combination of ingredients have been formulated and processed into a bilayer tablet. No immediate signs of incompatibility in the dosage form itself were evident. There is considerable flexibility in the tablet in terms of both composition, weight, and the weight of the layers, i.e. the slowly eroding later and the disintegrating layer. However, the concentration of emu oil that can be accommodated in this dosage form is 15% or less (based on the slow eroding layer). Incorporation of the lecithin was accomplished by dissolving the surfactant in the Emu oil. This approach required high temperature. However, alternative processing approaches were performed using low or no heat with slow mixing.

The oral care compositions of the present application containing emu oil, a soy lecithin emulsifying agent, one or more proteases, and one or more soluble calcium phosphate remineralizing agents is a multi-active composition. Without being bound by theory, the initial active component is the one or more proteases which quickly activate to remove dental plaque and wash away bacteria from the teeth of the subject. The soy lecithin emulsifying agent and soluble calcium phosphates form a complex with the emu oil. This complex allows for the soluble calcium phosphates and emu oil to remain in the mouth for an extended period of time, enhancing the effects of the composition. The emu oil coats the mouth of the subject, provides a soothing effect, and combats dry mouth. The soluble calcium phosphates remineralize the teeth of the subject.

When the oral care composition further contains one or more amino acids such as glutamine and/or arginine in the coating or outer layer, the coating or outer layer dissolves in the oral cavity prior to release of the one or more proteases and the soy lecithin-soluble calcium phosphate-emu oil complex. This embodiment provides an added effect of cellular repair, decreased inflammation and breakdown of mucus.

Overall, the oral care composition provides the following non-limiting benefits to the subject: removal of dental plaque, removal of bacteria from teeth, remineralization of teeth, reduction of dry mouth, increased feeling of comfort in, the mouth, cellular repair in the mouth, decreased inflammation in the mouth and breakdown of mucus in the mouth.

The bilayer tablet is described in FIGS. 1 and 2. The tablet consists essentially of a rapidly disintegrating layer containing the whitening/cleansing agent (i.e., carbamide peroxide) and a non-disintegrating slow eroding "lozenge-like" layer that contains the other components. The bilayer tablet creates a physical separation of the oxidizer from other product components in the dosage form. This feature is especially desirable considering that the peroxide may be incompantable with the other agents (i.e. papain).

When placed in the oral cavity, the saliva causes rapid disintegration of the disintegrating layer, creating a liquid environment with an effective level of free hydrogen peroxide. Simultaneously, the second layer, which contains the other components, including emu oil and the papain, begins to slowly erode. The duration of the whitening/cleansing action of the peroxide is relatively short, so exposure of the other component subject to oxidative degradation is limited and release of these ingredients is sustained.

REFERENCES

Abimosleh, S. M. et al. (2013) Emu oil reduces small intestinal inflammation in the absence of clinical improvement in a rat model of indomethacin-induced enteropathy. Evid Based Complement Alternat Med. 429706.

Abraham, J. (2008) Calcium phosphate mouth rinse for preventing oral mucositis. Commun Oncol. 5, 171-174.

Anneroth G, Nordenram G, Bengtsson S. (1980) Effect of saliva stimulants (Hybrin and malic acid) on cervical root surfaces in vitro. Scand J Dent Res. 88, 214-8.

Borges B. C. et al. (2010) Xerostomia and hyposalivation: a preliminary report of their prevalence and associated factors in Brazilian elderly diabetic patients. Oral Health Prev. Dent. 8, 2, 153-158, Cassolato S F, Turnbull R S. (2003) Xerostomia: clinical aspects and treatment. Gerodontology. 20, 64-77.

Chattopadhyay, S. (2014) Role of oral glutamine in alleviation and prevention of radiation-induced Oral Mucositis: A prospective randomized study South Asian J Cancer. 3(1), 8-12.

Chobotova, K. et al. (2010) Bromelain's activity and potential as an anti-cancer agent: Current evidence and perspectives. Cancer Lett. 290, 2, 1448-156.

Davies A N. (2000) A comparison of artificial saliva and chewing gum in the management of xerostomia in patients with advanced cancer. Palliat Med. 14, 197-203.

Hochberg M C, Tielsch J, Munoz B, et al. (1998) Prevalence of symptoms of dry mouth and their relationship to saliva production in community dwelling elderly: the SEE project. J Rheumatol 25, 486-4891.

Klimberg, V. S. et al. (1996) Glutamine suppresses PGE2 synthesis and breast cancer growth. J Surg Res. 63(1), 293-7.

Lindsay, R. et al. (2010) Orally administered emu oil decreases acute inflammation and alters selected small intestinal parameters in a rat model of mucositis. British Journal of Nutrition 104, 513-519

Masoudi Rad, H. (2014) Free amino acids in stimulated and unstimulated whole saliva: advantages or disadvantages. J Oral Rehabil. 41(10), 759-67.

Nederfors, T. (1996) Xerostomia: prevalence and pharmacotherapy. With special reference to beta-adrenoceptor antagonists. Swed Dent J Suppl. 116, 1-70.

Nederfors T, Isaksson R, Mornstad H, Dahlof C. (1997) Prevalence of perceived symptoms of dry mouth in an adult Swedish population-relation to age, sex and pharmacotherapy. Community Dent Oral Epidemiol, 25, 211-216.

Narhi T O, Meurman J H, Ainamo A. (1999) Xerostomia and hyposalivation: causes, consequences and treatment in the elderly. *Drugs & Aging* 15, 103-116.

Orellana M F, Lagravère M O, Boychuk D G J, Major P W, Flores-Mir C. (2006) Prevalence of xerostomia in population-based samples: a systematic review. Journal of public health dentistry 66, 2, 152-158.

Papas, A. S. et al. (2003) A prospective, randomized trial for the prevention of mucositis in patients undergoing hematopoietic stem cell transplantation. Bone Marrow Transplant 31, 705-712.

Scully C, Bagan J V. (2004) Adverse drug reactions in the orofacial region. Crit Rev Oral Biol Med. 15, 221-39.

Silvestre-Donat F J, Miralles-Jorda L, Martinez-Mihi V. (2004) Protocol for the clinical management of dry mouth. Med Oral. 9, 273-9.

Sonis, S. T. (2011) Oral mucositis. Anticancer Drugs. 7, 607-12.

Lu, X. et al. (2010) Linoleic acid suppresses colorectal cancer cell growth by inducing oxidant stress and mitochondrial dysfunction. Lipid Health Dis 9, 106.

What is claimed is:

1. An oral care composition in the form of a tablet comprising:
   a) 5-10% by weight emu oil;
   b) 1-5% by weight soy lecithin;
   c) 40 mg-60 mg of bromelain;
   d) 5-25% by weight amorphous calcium phosphate; and
   e) 1-5% by weight glutamine.

2. The composition of claim 1, further comprising canola oil, palm oil, sesame oil, safflower oil, soybean oil or sunflower oil.

3. The composition of claim 1, wherein the emu oil is Black emu oil.

4. The composition of claim 1, wherein the composition further comprises an isomalt.

5. The composition of claim 1, wherein the composition is formulated as a bilayer tablet or a multilayer tablet.

6. An oral care composition in the form of a tablet comprising:
   a) 5-10% by weight emu oil;
   b) 1-5% by weight soy lecithin;
   c) 40 mg-60 mg of bromelain;
   d) 5-10% by weight amorphous calcium phosphate; and
   e) 1-5% by weight glutamine.

* * * * *